(12) United States Patent
Campbell

(10) Patent No.: US 9,989,664 B2
(45) Date of Patent: Jun. 5, 2018

(54) PROCESS FOR MINING ALLUVIAL DEPOSITS

(71) Applicant: VDL Gold Pty Ltd, Melbourne, Victoria (AU)

(72) Inventor: John Gordon Mackay Campbell, Cremorne (AU)

(73) Assignee: VDL GOLD PTY LTD, Melbourne, Victoria (AU)

( * ) Notice: Subject to any disclaimer, the term of this patent is extended or adjusted under 35 U.S.C. 154(b) by 191 days.

(21) Appl. No.: 14/655,033

(22) PCT Filed: Dec. 24, 2013

(86) PCT No.: PCT/AU2013/001525
§ 371 (c)(1),
(2) Date: Jun. 23, 2015

(87) PCT Pub. No.: WO2014/100858
PCT Pub. Date: Jul. 3, 2014

(65) Prior Publication Data
US 2015/0346374 A1 Dec. 3, 2015

(30) Foreign Application Priority Data

Dec. 24, 2012 (AU) ................... 2012905695

(51) Int. Cl.
*G01R 1/30* (2006.01)
*G01V 3/20* (2006.01)
(Continued)

(52) U.S. Cl.
CPC ............ *G01V 3/20* (2013.01); *E02F 3/8866* (2013.01); *E02F 3/907* (2013.01); *E21B 47/00* (2013.01);
(Continued)

(58) Field of Classification Search
CPC .. G01R 27/2605; G01R 19/0092; G01R 1/30; G01R 15/16; G01R 19/0084;
(Continued)

(56) References Cited

U.S. PATENT DOCUMENTS 3,214,728 A * 10/1965 Higgins ................... G01V 3/02
340/852
3,728,622 A * 4/1973 Williams ................. G01V 3/06
324/71.1
(Continued)

FOREIGN PATENT DOCUMENTS

CA 1215743 A 12/1986
CA 1215743 A1 12/1986
(Continued)

OTHER PUBLICATIONS

Examination Report received in Chinese Application No. 2013800734757 dated Jan. 9, 2017.
(Continued)

*Primary Examiner* — Jermele M Hollington
*Assistant Examiner* — Taqi Nasir
(74) *Attorney, Agent, or Firm* — Knobbe, Martens, Olson & Bear, LLP

(57) ABSTRACT

Disclosed herein is a remote operating vehicle (ROV) for use in a subterranean mining process, such as to extract material from beneath a rock layer. The ROV may be provided as a number of components each including their own umbilical cord. Each of the components may be lowered through a borehole and assembled together to form the ROV underground. Also disclosed herein is a device and method for in-line monitoring of a mining material to determine the presence of a material of interest in the mining material. The device includes conductive plates that are spaced apart. The device detects the presence of a material (Continued)

of interest as it passes through the spacing between the conductive plates.

22 Claims, 8 Drawing Sheets

(51) Int. Cl.
    *E21C 41/00*     (2006.01)
    *E21B 47/00*     (2012.01)
    *E02F 3/88*     (2006.01)
    *E02F 3/90*     (2006.01)
    *G01N 27/04*     (2006.01)
    *E21C 39/00*     (2006.01)
    *B63C 11/52*     (2006.01)
    *G01N 33/24*     (2006.01)

(52) U.S. Cl.
    CPC .............. *E21C 39/00* (2013.01); *E21C 41/14* (2013.01); *G01N 27/041* (2013.01); *B63C 11/52* (2013.01); *G01N 33/24* (2013.01)

(58) Field of Classification Search
    CPC ........ G01R 21/00; G01R 27/02; G01N 15/06; G01N 2015/0053; G01N 33/2835; G01N 33/2858; G01N 33/18; G01N 33/2823; G01N 33/30
    USPC ..... 324/71.1, 446, 553, 722, 686, 754, 71.4, 324/65 R; 73/53.05, 53.07, 61.42, 61.71
    See application file for complete search history.

(56) References Cited

U.S. PATENT DOCUMENTS

| | | | |
|---|---|---|---|
| 4,419,135 A | 12/1983 | Hoge | |
| 4,635,735 A * | 1/1987 | Crownover | E21B 21/067 175/42 |
| 5,596,266 A * | 1/1997 | Mori | G01N 15/1031 324/446 |
| 5,763,795 A * | 6/1998 | Tanaka | G01N 33/493 324/439 |
| 5,950,732 A * | 9/1999 | Agee | C10G 2/30 166/248 |
| 6,178,670 B1 | 1/2001 | Susman et al. | |
| 6,236,212 B1 | 5/2001 | Wynn | |
| 2002/0030398 A1 | 3/2002 | Drake et al. | |
| 2004/0091095 A1* | 5/2004 | Weaver | H04M 3/42229 379/211.02 |
| 2008/0030398 A1 | 2/2008 | Nakamura | |
| 2010/0284748 A1* | 11/2010 | Graham | E21D 9/04 405/146 |
| 2012/0082892 A1* | 4/2012 | Kobayashi | H01M 4/134 429/211 |

FOREIGN PATENT DOCUMENTS

| | | |
|---|---|---|
| CA | 2363748 C | 4/2006 |
| CA | 2654659 A1 | 8/2009 |
| CN | 101270672 A | 9/2008 |
| CN | 101545366 A | 9/2009 |
| EP | 0184720 A1 | 6/1986 |
| GB | 2438405 A | 11/2007 |
| WO | 1999007949 A1 | 2/1999 |

OTHER PUBLICATIONS

First Examination Report, dated Feb. 3, 2017, received in New Zealand Application No. 709095.

International Search Report & Written Opinion, dated Mar. 31, 2014, in International Application No. PCT/AU2013/001525.

Supplementary European Search Report dated Jul. 1, 2016 in Application No. EP 13866966; 8 pages.

* cited by examiner

PROCESS FOR MINING ALLUVIAL DEPOSITS

FIELD OF THE INVENTION

The invention relates to underground mining operations conducted beneath a rock layer.

BACKGROUND OF THE INVENTION

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

Drilling to detect gold-bearing alluvium beneath the basalt cover has, for over 100 years, been the only means of prospecting for deep leads. These holes, usually diamond drilled, provide little data other than the thickness of basalt cover and alluvium, and the depth of bedrock. The presence of gold was often not able to be determined.

Determining the location and boundaries of deep lead gold deposits and the assessment of their economic potential is difficult, and the results are considerably less definitive than for many other types of mineral deposits.

Generally speaking, for a deep lead, the mineralised target zone is narrow relative to the breadth of the original valley floor, and more so compared with the width of the basalt sheet which later flooded the valley, sometimes obscuring it entirely. It is impossible therefore, to use surface geological evidence to trace the course of the narrow and sinuous river bed which carries the auriferous gravel deposits. The only practical means of exploration has been the drilling of lines of holes across the presumed likely course of the lead. This is effective in outlining the general profile of the original valley floor, and in locating thicker accumulations of wash. However, the cost of a drill pattern of sufficiently close spacing to detect bedrock gutters of only a few tens of meters width has been regarded as prohibitive.

The general experience of using drill-hole results to determine gold concentrations in the wash has proved quite unreliable. To penetrate the basalt cover, small diameter drilling (200 mm and less) has had to be used. Holes of this size provide a sample volume much too small for reliable grade determination in poorly consolidated gravel and sand which contains coarse gold particles. The larger gold grains are often not recovered by the drilling method and frequently, results appear to have understated even the local grades within a deposit. Modern exploration geophysical methods have been applied with mixed success in determining depths of basalt and bedrock in deep lead areas.

The distribution of gold particle size along the trend of the lead is of significance in assessing the likelihood that the lead may have been charged at several points along its course with gold derived from tributary streams, or from bedrock reef outcrops which it may have traversed. Geologically, the introduction of gold at various points along its course is expected to be considerably more favourable for the downstream persistence of economic concentrations, than if the only source was at the head of the lead.

Any mining method which proposes to exploit these deep lead deposits will have to operate through a depth of cover of up to 120 m. Most commonly this consists of fairly competent and free-standing basalt. The immediate hanging wall to the gold bearing wash is often a poorly consolidated and heavily water-bearing section, in the range of up to 100 m thick, of sand and clay which carries little, if any gold. The specially developed underground mining methods of the early miners were able to extract the thin (0.5 to 1.5 m) layer of gold bearing wash without suffering significant dilution from these overlying sand and clay beds. The development of a method which can profitably mine these deeps leads without the requirement for intensive underground labour would constitute a major technological advance.

A number of methods have been proposed for mining from boreholes. The basis of these has generally been the use of water-jets to break up the alluvium and the pumping the resulting slurry to the surface. The problem with these systems is basically one of cost. In an unconsolidated deposit such as a Deep Lead the lower grade roof will feed into the cavern. This means that a large volume of "overburden" will be extracted to extract a small volume of wash. The water jet is likely to have a short range as it is operating in water which will disperse the force. The net result is that a large number of boreholes are required to extract the wash and the economics are unlikely to be favourable. Furthermore, there are environmental pressures which limit the types of methods that can be employed to extract the gold—regardless of how safe a process could be proven to be in many cases they are unacceptable to the local community.

In light of the above, it would be advantageous to have mechanisms for extracting desirable minerals from underground alluvial deposits that are contained beneath a rock layer, such as a basalt layer.

SUMMARY OF THE INVENTION

There are a number of potential options for extraction of a mineral from mineral containing alluvial deposits. However, many of these options are not practical for environmental, economic, or public perception reasons. Thus in one aspect, the present invention is directed towards an alternative method of extracting mineral containing alluvial deposits using a deep lead suction dredging process. Preferably the mineral contained in the alluvial deposits is gold.

In one aspect of the invention there is provided a method of extracting alluvial deposit from an underground source beneath a rock layer, the method including: drilling a bore hole through the rock layer; extracting some of the alluvial deposit from beneath the rock layer to form an excavated zone; lowering at least two components into the excavated zone, each component having an umbilical; assembling the at least two components into a remote operated vehicle (ROV); using the remote operating vehicle to mine the alluvial deposit and provide the mined alluvial deposit to the surface via at least one of the umbilicals.

Preferably the rock layer is a hard rock layer. For example the rock layer may be a basalt layer or another rock formed from solidified lava, or other rock layer that restricts access to an alluvial material contained beneath it.

Preferably the bore hole has a diameter of around 1.8 m.

Preferably at least three components are lowered into the excavated zone and are assembled into the ROV.

Preferably the mined mineral alluvial deposit is processed at a processing plant on the surface to extract the material of interest, resulting in a mineral depleted alluvial material. More preferably, at least some of the mineral depleted alluvial material is returned and used to backfill the excavated zone.

In another aspect of the invention there is provided a remote operated vehicle (ROV) for use in an underground mining of an alluvial deposit from beneath a rock layer, the remote operated vehicle including: at least a first component having a first umbilical, the first component sized to fit down a borehole; and a second component having a second umbilical, the second component sized to fit down the borehole; wherein the first and second component are configured to be joined together in an excavated region beneath the rock layer to form the remote operated vehicle.

ROVs have been used in underwater environments for recovery of bed materials, such as sea bed materials in the case of an undersea ROV. The following discussion is in relation to undersea ROVs, but is equally applicable to general underwater ROVs. Undersea ROV's are generally not suitable for use in underground environments. Firstly, the excavated region of an underground environment is not necessarily flooded with water, as many of the undersea ROV's are designed for propulsion through water, these ROVs are not adapted for use in an environment that is not flooded. Secondly, an underground environment that is flooded with water will contain a large amount of suspended solids from the mining and excavation process as compared with a undersea environment in which the ROV is mostly operating in seawater that has a very low concentration of suspended solids. The, water in an underground excavated region is likely to be in the form of a particulate laden solution, such as a slurry or an alluvial slurry. The ROV must therefore be capable of operation in an aqueous environment that is laden with particulate material or is a slurry.

Furthermore, undersea ROV's are not generally limited in terms of size. The ROV is either a unitary device or can be assembled on the deck of vessel or platform before being lowered into the ocean. There is no need to assemble the ROV from constituent components undersea. Moreover, the ROV can more easily and simply be assembled above the water prior to being lowered into the water.

In contrast, ROV's that are operated beneath a rock layer in an underground environment may have size limitations placed upon them. In order to access an underground alluvial deposit that is beneath a rock layer, a borehole is drilled through the rock layer. Boreholes are expensive and time consuming to produce. Therefore, the inventor has determined that it can be advantageous to minimise the diameter of the borehole and still be able to mine a deposit under a rock layer with an ROV if one lowers constituent components of an ROV through the borehole and then assembles the ROV underground, for example in an excavated region beneath the rock layer. Together these components are assembled to form an operable ROV that can be used to mine and extract alluvial deposits from underground. As the ROV is lowered in a number of pieces which are sized to fit through the borehole, the size of the ROV once it is assembled underground is larger than the borehole in at least one dimension.

Thus, preferably once at least the first and second components have been assembled together, the ROV has a size that is greater than either the first or the second components. For example, an outer dimension, such as a width or a length, of the ROV is greater than a corresponding outer dimension of the first or second components. More preferably, the volume bounded by the periphery of the ROV is greater than a volume bounded by either of the first or the second components.

In an embodiment, the ROV is operable to extract an alluvial deposit only once the first and second components have been joined together.

Preferably the at least two components are assembled by bolts or snap links.

Preferably the first component includes the drive mechanism, and the second component includes the dredging and/or mining equipment.

In an alternative arrangement at least three components are lowered into the excavated zone and are assembled into the ROV; the first component, the second component, and a third component. In this alternative arrangement, it is preferred that, the first component and the third component are a left hand and right hand drive mechanism of the ROV and the second component includes the dredging and/or mining equipment. Even more preferably, the first component and the third component are assembled on to the second component. In another aspect of the invention there is provided a remote operated vehicle for use in underground mining of an alluvial deposit from beneath a rock layer, the remote operated vehicle sized to fit down a borehole including: an umbilical, a plurality of ground engaging drive mechanisms which preferably include at least two pairs of ground engaging drive mechanisms, wherein the ground engaging drive mechanisms are operable in a first mode (e.g. such as in the same direction) to propel the vehicle, and are operable in a second mode (e.g. such as in opposing directions) to displace the alluvial deposit from an underlying rock layer, suction means to extract the displaced alluvial deposit and provide the displaced alluvial deposit to an above ground reservoir via the umbilical.

The two pairs of ground engaging mechanisms may for example be a front pair of ground engaging mechanisms and a rear pair of ground engaging mechanisms. The front and rear pairs of ground engaging mechanisms are operable in the same direction to propel the vehicle in a desired direction (such as forward or backward). However, the front and rear pairs of ground engaging mechanism are also operable in opposing directions. For example, the front pair of ground engaging mechanisms is operated in one of the forward or the backward direction and the rear pair of ground engaging mechanisms is operated in the other of the forward or the backward direction. The effect of this operation is that the ground engaging mechanisms provide a grinding effect on the surface with which the ground engaging mechanisms are engaged. This liberates or displaces an alluvial deposit from an underlying rock layer, which results in the alluvial deposit being more easily extracted, for example through a dredging or suction process.

It will be understood that, in this example, the front pair of ground engaging mechanisms and the rear pair of ground engaging mechanisms are operable in opposing directions at different rates. This allows the ROV to be operated so that it can move in the forward or reverse directions while also providing a grinding effect on the surface with which the ground engaging mechanisms are engaged. By way of example, the front pair of ground engaging mechanisms may be operated in the forward direction at greater speed or torque than the rear pair of ground engaging mechanisms which are operated in the reverse direction. The effect of this is that the ROV moves in the forward direction even though the rear pair of ground engaging mechanisms are operated in the reverse direction. In this way, the rear pair of ground engaging mechanisms provide a grinding effect to the surface beneath the ROV to liberate or displace alluvial deposit from the underlying rock layer.

It will be understood that reference to the front pair of ground engaging mechanisms and the rear pair of ground engaging mechanisms is illustrative only. The ROV may instead include two side pairs of ground engaging mechanisms, such as a right hand side pair of ground engaging mechanisms, and a left hand side pair of ground engaging mechanism. Each of the right hand side pair and left hand side pair are operable in the right or left hand directions to result in the effect described above.

In respect of the above two aspects directed toward the ROV, it is preferred that the drive mechanism is selected from the group consisting of tracks, wheels, or screw-propulsion for movement over a surface.

In another aspect of the invention there is provided a remote operated vehicle for use in an underground mining of an alluvial deposit from beneath a rock layer, the remote operated vehicle including: a plurality of components sized to fit down a borehole, each component having an umbilical, and wherein each component is configured to be joined together in an excavated region beneath the rock layer to form the remote operated vehicle.

It is preferred that at least one of the plurality of components contains the mining equipment and at least one of the plurality of components includes the drive mechanism. More preferably the ROV includes multiple drive mechanism components that may be the same or different, e.g. each drive mechanism is independently selected from the group consisting of tracks, wheels, or screw-propulsion for movement over a surface. In this way, an ROV may include 2, 3, 4, or more drive units that may be the same or different. One or more of the drive units may be engaged in moving the vehicle, while one or more are engaged in an operation to displace alluvial material e.g. brushing, sweeping, or excavating alluvial material. In respect of the above three aspects directed toward the ROV, it is preferred that the ROV is amphibious and can perform the dredging/mining operation in an underwater environment. More preferably, the ROV includes aqueous propulsion means selected from the group consisting of a propeller, fins, or water-jet.

In respect of the above three aspects directed toward the ROV, it is preferred that the ROV includes a waste pipeline for depositing a mineral depleted alluvial material, or an alluvial deposit with a low mineral concentration in a backfill location underground beneath the rock layer.

In respect of the above three aspects directed toward the ROV, it is preferred the ROV includes a water cannon and/or mechanical cutter for breaking up the mineral alluvial deposit and/or to alter the consistency of the mineral alluvial deposit to create a slurry.

In respect of the above three aspects directed toward the ROV, it is preferred that the ROV includes a fail-safe mode, wherein when communications between an operator and the ROV are no longer possible a safety mechanism is deployed. More preferably, the safety mechanism is an airbag (or flotation bag) type system, which when deployed, lifts the ROV from the floor of the excavated region.

In respect of the above three aspects directed toward the ROV, it is preferred that the ROV includes survey means. Preferably the survey means is selected from the group consisting of sonar, ultrasound, optical camera, or combinations thereof.

In another aspect the present invention provides a method for supporting a rock layer overlying an excavated region. The method includes, forming one or more support structures between a base of the excavated region and a ceiling of the rock layer for supporting the rock layer above the excavated region.

Preferably forming the one or more support structures includes injecting a settable material to form at least one support structure in situ. The method can also include reinjecting material excavated from the cavity into the cavity. In a one preferred embodiment the method includes reinjecting material excavated from the cavity into the cavity, and forming support structures in said reinjected material.

In some cases the method can involve using said settable material as a binder mixed with another material to form one or more composite support structures. The settable material and other material can be mixed prior to injection of them into the cavity. Alternatively the settable material can be injected directly into the other material in situ where a support structure is to be formed.

Reinjection of either or both of settable material or material excavated from the cavity, can be performed from the surface to a site of a support structure to be formed. Alternatively, reinjection of either or both of settable material or material excavated from the cavity, can be performed using a remotely operated vehicle located within the cavity. Both techniques could be used together at the one site.

The method may include providing a mould, form or container to contain the settable material prior to hardening, said mould, form or container being left in place after hardening. For example the mould, form or container is a bag or the like that is filled with settable material.

Support structure can be of any type, such as a support pillar, support block, or structure of an amorphous shape.

In another aspect of the invention, there is provided a method for supporting a rock layer overlying an excavated, the method including: forming one or more support pillars between a base of the excavated region and a ceiling of the rock layer using a remote operated vehicle, the pillar or pillars supporting the rock layer above the excavated region. Preferably, the ROV is an ROV as previously described.

At least a component material from which the pillars are formed may be provided from the surface via an umbilical of the ROV. For example, a settable material such as cement may be supplied from the surface to the ROV where the ROV applies the material at an appropriate location. In certain embodiments, excavated alluvium is used as aggregate combined with the settable material to form composite pillar(s). In a preferred form, where the settable material is cement, a portion of the excavated alluvium can be combined with the cement to form concrete pillars. This may be the case where the excavated alluvium is found to be too low in the material of interest, instead of transporting this alluvium to the surface it can be used to form the support pillars. Alternatively, or additionally, depleted alluvium (which has had the material of interest at least partially removed) may be recycled as a composite constituent and returned via the umbilical to the ROV for use in the support pillar. In certain embodiments the pillars can comprise a containment envelope, e.g. a bag, tube or the like, that acts as a form work to hold the settable material. In one form, this could take the form of plastic bags filled with concrete.

In another aspect of the invention there is provided a pipe for use in underground mining of an alluvial material from beneath a rock layer, the pipe including: a debris trap portion, wherein the debris trap portion has a closed state for transporting the alluvial material and trapping large debris, and an open state for releasing the trapped debris.

In an embodiment the trap portion of the pipe further includes hinges arranged along the longitudinal axis of the pipe, wherein the debris trap portion can be split open along the longitudinal axis to release the trapped debris.

In an alternative embodiment the trap portion further includes hinges arranged in such a manner that the debris trap portion of the pipe opens radially outward to release trapped debris.

In both of the above embodiments it is preferred that the hinges include a tab that has a locked position and an unlocked position, wherein when the tab is in the locked position the debris trap portion is locked in the closed state, and when in the tab is in the unlocked position, the debris trap portion may be moved into the open state. More preferably the tabs can be actuated by fluid flow that is in the reverse direction to the direction of transport of the alluvial material.

Preferably the debris trap portion is selected from the group consisting of a U-bend, S-bend, J-bend, or P-bend. More preferably, the trap portion is a U-bend.

Preferably, the pipe includes a screen on an inlet.

In another aspect of the invention there is provided a suction dredge including: a dredge pump; a suction pipe; a debris trap in fluid communication with the suction pipe, the debris trap including a tortuous flow path; wherein the debris trap is reconfigurable between an operable condition in which it defines a flow path in fluid communication with the suction pipe in through which dredged material may be sucked and being sized to capture oversized objects; and an inoperable condition in which the flow path is opened to release trapped objects.

Preferably the suction dredge includes an ROV as previously defined, the ROV connecting between the dredge pump and the suction pipe.

In another aspect of the invention there is provided a device for in-line monitoring of a mining material from a mining process, the device including: at least two conductive electrodes separated by a non-conductive spacer, the conductive electrodes arranged so as to overlap at least a portion of the non-conductive spacer, the overlap defining a spacing between the two conductive electrodes through which alluvial material can pass, the conductive electrodes configured to detect the presence of a material of interest in the alluvial material as it passes therethrough.

Preferably the conductive electrodes are plate shaped.

In another aspect of the invention there is provided a method for in-line monitoring of the concentration of a material of interest in a mining material obtained from a mining process, the method including: providing at least one device as defined above within a flow path for transporting the mining material, passing at least some of the mining material through the spacing between the two conductive electrodes, and determining the presence of the material of interest in the mining material.

In yet another aspect of the invention there is provided an in-line monitoring device for detecting a material of interest in a mining material, the device including: a plurality of electrodes including at least a first electrode which is a positive or a negative electrode, and second and third electrodes which are opposite in charge from the first electrode, the first electrode being separated from the second and third electrodes by a non-conductive space or spaces through which mining material can pass, the device configured to detect the presence of the material of interest in the mining material as it passes through the space and forms an electrical connection between the first electrode and at least one of the second or third electrodes.

Preferably the first electrode is configured to form with each of the second and third electrodes a different electrical circuit. Thus when a material of interest forms an electrical connection between the first electrode and the second electrode, a first electrical circuit is established, and when a material of interest forms an electrical connection between the first electrode and the third electrode, a second electrical circuit is established. In this way, it is possible to determine the spatial location of the particle on detection by identifying which circuit has been activated. Furthermore, if there is different electrode spacing between the first electrode and the second electrode as compared with the first electrode and the third electrode (as will be discussed in more detail) size information on the material of interest can be obtained.

Furthermore, this arrangement avoids an issue which can arise where particles become lodged between electrodes. Often conductive particles become lodged and are entrapped between a pair of electrodes. In some instances, the particle will remain lodged there until it is manually removed, for example during a cleaning or servicing operation. If the electrodes are arranged in a single circuit, the presence of the entrapped conductive particle could cause the sensor to malfunction, as the sensor would continue to generate a signal identifying the presence of a conductive particle as long as the jammed particle remained lodged between electrodes. Furthermore, as the pairs of electrodes have been arranged on separate electrical circuits, a false positive signal resulting from the jammed particle may be removed or filtered out electronically or via software.

In an embodiment, the electrodes are arranged in a stack, with the first electrode being located at a first distance in the stack from the second electrode and at a second distance in the stack from the third electrode, the first distance being less than the second distance. Preferably the electrode stack there are more than three electrodes in the plurality of electrodes. More preferably, the electrode stack includes more than four electrodes. Even more preferably, the electrode stack includes more than ten electrodes. In preferred embodiments the electrode stack includes a multiplicity of electrodes, for example the stack may be between 10 mm and 500 mm in height and contain electrodes spaced from their immediate neighbour by between 5 micrometers and 2000 micrometers. Embodiments may have neighbouring electrodes spaced apart by between 10 micrometers and 1000 micrometers. Most preferably neighbouring electrodes are spaced apart by between 50 and 200 micrometers. In one embodiment electrodes are spaced apart by around 100 micrometers.

This is advantageous as the device is configured to detect a material of interest having a size in at least one dimension corresponding to the first axial distance such that the material of interest forms an electrical connection between the first electrode and the second electrode, and the device is configured to detect a material of interest having a larger size in at least one dimension corresponding to the second axial distance such that the material of interest forms an, electrical connection between the first electrode and the third electrode.

Preferably the first electrode forms a first circuit with the second electrode, and the first electrode forms a second circuit with the third electrode, the first and second circuits being electrically separated from each other. In this way, the device is configured to detect and report on approximate sizes of the material of interest in the mining material. In an example, a device includes a first positive electrode arranged in stacked relation with a second and third negative electrodes. The first and second electrode form a first circuit which is separate to a second circuit formed between the first and third electrode. The spacing between the first electrode and the second electrode is 100 μm, and the spacing between the first electrode and the third electrode is 200 μm. A material of interest having a size of 150 μm in one dimension will bridge the gap between the first electrode and the second electrode activating the first circuit, but will not bridge the gap between the first and the third electrodes. However, a material of interest having a size of at least 200 µm in one dimension will bridge the gap between the first electrode and the third electrode activating the second circuit. Therefore, depending on which circuits are activated, and based on the space between the electrodes, it is possible to determine a size distribution of the material of interest in the mining material. Increasing the number of electrodes and potential circuits in a stack and having more varied spacing between electrodes on the stack will enhance the resolution of the detector and provide a better estimate as to the size distribution of the material of interest in the mining material.

Preferably, the second and third electrode are electrically separated but adjacent electrodes. The second and third electrodes may for example be electrically separate by a non-conductive separation element such as an insulation layer, or may be separated by a non-conductive space or spacer to electrically isolate the second and third electrodes from each other.

Preferably, the electrodes are in a stepped arrangement, with the third electrode overhanging the second electrode to form the space, the size and shape of the space configured to minimise entrapment of the material of interest and/or mining material.

Preferably electrodes separated by smaller spaces are arranged inwards of electrodes separated by larger spaces. Where the outwards direction is the direction from which the mining material is presented to the electrodes. In this way, larger particles of material of interest are prevented from bridging the more inward smaller spaces between electrodes to minimise double counting of material of interest.

In an embodiment, a non-conductive spacer or spacers defines the space or spaces, and the plurality of electrodes are arranged so as to overlap at least a portion of the non-conductive spacer or spacers, the overlap defining the space or spaces between at least the first electrode and the second and third electrodes.

In an embodiment, the in-line monitoring device includes a plurality of positive and negative electrodes, the positive and negative electrodes separated from each other by the non-conductive spacers.

In an embodiment, the plurality of electrodes are a plurality of conductive plates. In an arrangement of this embodiment, the plurality of plates are in stacked relation with each other, the non-conductive spacer being a non-conductive plate located between adjacent conductive plates of opposite charge, and wherein adjacent plates of the same charge are electrically separated. Preferably the edges of the conductive plates are bevelled. The inventor has found that the bevelled surfaces assist in preventing particles from lodging between the conductive plates.

In an embodiment, the first electrode has a first face which faces a corresponding face of at least one of the second electrode or the third electrode. The faces spaced apart by a non-conductive space and arranged so that mining material can flow there-between. Preferably the first face and the corresponding face each have a surface area that allows an electrical connection to be formed in the presence of the material of interest for sufficient time that an electrical signal can be generated and detected. Preferably, the surface area is from about 0.008 m$^2$ to about 3.2 m$^2$. More preferably, the surface area is from about 0.13 m$^2$ to about 1.54 m$^2$. Even more preferably, the surface area is from about 0.5 m$^2$ to about 1.13 m$^2$.

In an embodiment, the non-conductive spacer is a portion of a flow channel through which the mining material is transported.

In an embodiment, the plurality of electrodes are mounted to an outer wall portion of the flow channel.

In an embodiment, the plurality of electrodes each include an aperture (403A), and the device further includes a non-conductive shaft, the non-conducting shaft extending through the apertures, and the plurality of electrodes being mounted to the non-conductive shaft.

In an embodiment, the plurality of electrodes are each formed from a material having a hardness of at least 7 on the Mohs scale, but most preferably is greater than 9. The hardness of the electrodes can be selected based on the minerals present in the deposit being analysed. In an alternative embodiment, the plurality of electrodes are each formed from a resilient material, e.g. material having Shore durometer harness of about D100 or less as defined in ASTM D22400-00. Such electrodes resist damage by yielding In an embodiment, the non-conductive space can be formed from a material having a hardness similar to that of the electrodes with which they are used.

In another aspect of the invention there is provided the use of a device as previously defined in an in-line monitoring process for detecting a material of interest in a mining material.

In another aspect of the invention there is provided the installation of a device as previously defined in a flow channel for transporting a mining material.

In a further aspect of the invention there is provided a method for in-line monitoring of a mining material to detect a material of interest in the mining material, the method including: providing a device as defined previously in a flow stream of a mining material; and using the device to monitor for a material of interest in the mining material.

In an aspect of the invention, there is provided an in-line monitoring process for detecting a material of interest in a mining material, the process including: providing a device to a flow channel for the mining material, the device including: a plurality of electrodes including at least three electrodes, a first electrode which is a positive or a negative electrode, and second and third electrodes which are opposite in charge from the first electrode, the first electrode being separated from the second and third electrodes by a non-conductive space through which mining material can pass, the device configured to detect the presence of the material of interest in the mining material as it passes through the space and forms an electrical connection between the first electrode and at least one of the second or third electrodes transporting the mining material through the flow channel so that at least a portion of the mining material passes through the space; and monitoring the portion of the mining material for the material of interest.

In an embodiment, the step of monitoring further includes providing an output signal having a value that is indicative of the relative concentration of the material of interest in the mining material, wherein the value of the output signal is compared against a baseline value, and if the output signal is below the baseline value the mining material is discarded, and if the output signal is above the baseline value the mining material is retained. Preferably, the value of the output signal is used to determine a downstream mining process.

In an embodiment, wherein the device is provided on both; an inlet stream to a mining process and an outlet stream from the mining process. Preferably, the device on the inlet stream provides an inlet signal which is indicative of the relative concentration of the material of interest in the inlet stream, and the device on the outlet stream provides an outlet signal which is indicative of the relative concentration of the material of interest in the outlet stream; wherein the inlet signal and the outlet signal are correlated so as to provide an indication of an efficiency for extraction of the material of interest from the mining material.

In an arrangement of this embodiment, the inlet stream to the mining process is at a location near to an extraction site of mining material, and the outlet stream from the mining process is at a processing site where the material of interest can be extracted from the mining material.

It is intended that the in-line monitoring can be applied on an inlet flow path to a process, an outlet flow path from a process, or an intermediate flow path within a process. The term inlet is intended to encompass an inlet to the overall process, or an inlet to a unit process. Similarly, the term outlet is intended to encompass an outlet from the overall process or an outlet from a unit process.

Preferably the flow path is a pipe, a hose, or an open flow channel.

Further aspects of the present invention and further embodiments of the aspects described in the preceding paragraphs will become, apparent from the following description, given by way of example and with reference to the accompanying drawings.

DETAILED DESCRIPTION OF THE EMBODIMENTS

The invention relates to the extraction of minerals from alluvial deposits that are located underground, beneath a rock layer. Alluvial material or alluvial deposits includes loose, unconsolidated soil or sediments of which clay, gravel, sand, and/or silt are examples. The rock layer may for example be a layer of basalt that has formed from volcanic activity where basaltic lava has flowed over an area containing an alluvial mineral deposit, and has cooled and solidified over the top of the alluvial mineral deposit. The alluvial mineral deposits beneath this rock layer may contain a number of valuable minerals, such as gold. However, as the alluvial deposits are trapped beneath a rock layer, they are difficult to access and extract. Furthermore, the alluvial deposits may be located below the water table, so any excavation of the alluvial deposits can lead to the excavated region filling with water.

Broadly, the overall process (termed Deep Lead Suction Dredging) comprises: (i) drilling a borehole through the rock layer, (ii) excavating a region underneath the rock layer by removing some of the mineral containing alluvial material via a dredging process, (iii) lowering a remote operated vehicle into the excavated region, (iv) extracting the mineral containing alluvial material with the remote operated vehicle (ROV), (v) processing the extracted alluvial material to recover the mineral. Some or all of the waste alluvial material (e.g. mineral-depleted alluvial material) can then be returned underground e.g. via the ROV, or could be sold as sand and/or gravel. The invention is also directed to ancillary mining support processes such as detection of the material of interest in the alluvial deposit, and the use of this detection mechanism as a process control tool.

Figure 1:
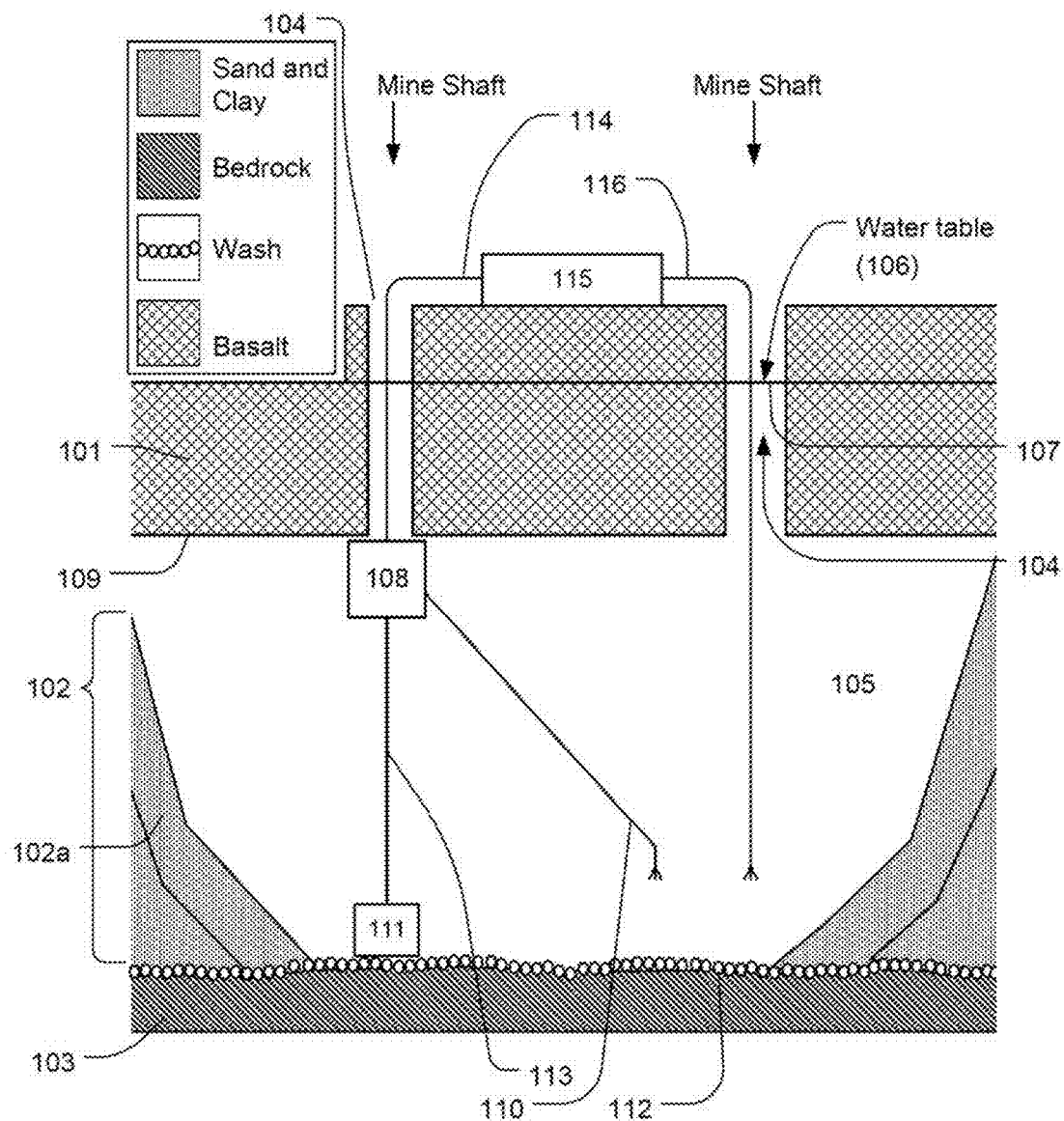
FIG. 1 provides an illustration of the overall ROV dredging process.

FIG. 1 provides an illustration of the process. In this embodiment, a basalt layer 101 overlies a gold containing alluvial deposit 102, which sits on top of bedrock 103. A borehole 104 is drilled through the basalt layer 101 and an excavated area 105 is partially formed by dredging gold containing alluvial material from beneath the basalt layer 101. As the excavated area 105 is below the water table 106, the excavated area 105 fills with water 107. The dredging process can initially be done by a surface pumping apparatus; however an additional subsurface pumping station 108 may be provided adjacent to the underside or roof 109 of the basalt layer 101, having a suction line 110 for dredging the alluvial material. An ROV 111 is lowered through a borehole 104 and assembled underground in situ if required. The ROV 111 has an umbilical 113 which provides power, hydraulics, water, suction, control etc. The ROV 111 grinds alluvial deposit 102 to free alluvium 102a from the it. This freed alluvium 102a and general wash alluvium 112 is then extracted via suction through the umbilical 113 or the suction line 110. This material is then passed via a pipeline 114 to a gold plant 115 for treatment. Gold is extracted from the alluvium. The gold-depleted alluvium can then be returned to the excavated area 105 by way of a return pipeline 116. Some of the gold-depleted alluvium may be retained and sold as filler material, e.g. sand or gravel.

As discussed above, on identification of a suitable mining location, one of the first steps is to drill a borehole through the rock layer to provide access to the mineral containing alluvial material. For practical and economic reasons the diameter of this hole is typically limited to about 1.8 m (approximately 6 feet). However, if necessary this shaft could be enlarged to any required size. The shaft may have to be lined to prevent cross aquifer flow or to address the potential issue of shaft collapse (which will depending on the structural characteristics of the rock layer).

Once access to the alluvium has been achieved the next stage is to clear enough alluvium such that there is an excavated region in which the ROV is able to move freely. This can be done by the ROV itself or by suction pumps similar to those used in borehole mining. The ROV can then be lowered through the borehole in to the excavated region.

ROV's are used in offshore dredging or piping operations. ROV's are provided as single components that can be loaded off a ship, and are generally provided at the size required for the intended operation. In contrast, one aspect of the present invention is directed to the use of an ROV in an on-shore subsurface application. In this application, the size of the ROV is limited by its intended operation (e.g. subterranean mining).

The necessity for the ROV to go down a shaft limits the size of the ROV. This will require consideration of the size/capability and operating cost of the ROV versus the cost of the shaft. Furthermore, as the size of the ROV is restricted by the size of the shaft passing through the rock layer, the ROV can be designed to go down the shaft in sections, and be assembled underground. Ideally the ROV consists of two or more components that can be assembled beneath the rock layer.

In an embodiment, the ROV is divided into three separate components—left and right components that include the wheels, tracks, screw propulsion, or other drive mechanism of the ROV, and a central component that contains the dredging and mining equipment. The first and second parts are assembled onto the third part, and this may be via bolts, snap links, or other suitable attachment mechanisms. Depending on the size of the ROV required for the operation, and the specific mining requirements of the particular site, the ROV may include two separate components, or may include more than three separate components.

The ROV will also be supplied with an umbilical. The umbilical can be used for a variety of purposes, such as to control the ROV, to supply power to the ROV (whether electrical or hydraulic), to provide a mode of communication with the ROV, to provide water to the ROV, or to extract dredged material from the ROV. It is important to note that the ROV may also include wireless means of communication. In a preferred arrangement, each separate component of the ROV will be provided with its own umbilical. That is, in the case where the ROV consists of multiple separate components that are assembled in-situ in the excavated region beneath the rock layer, a plurality of these separate components is provided with its own umbilical.

Figure 2A:
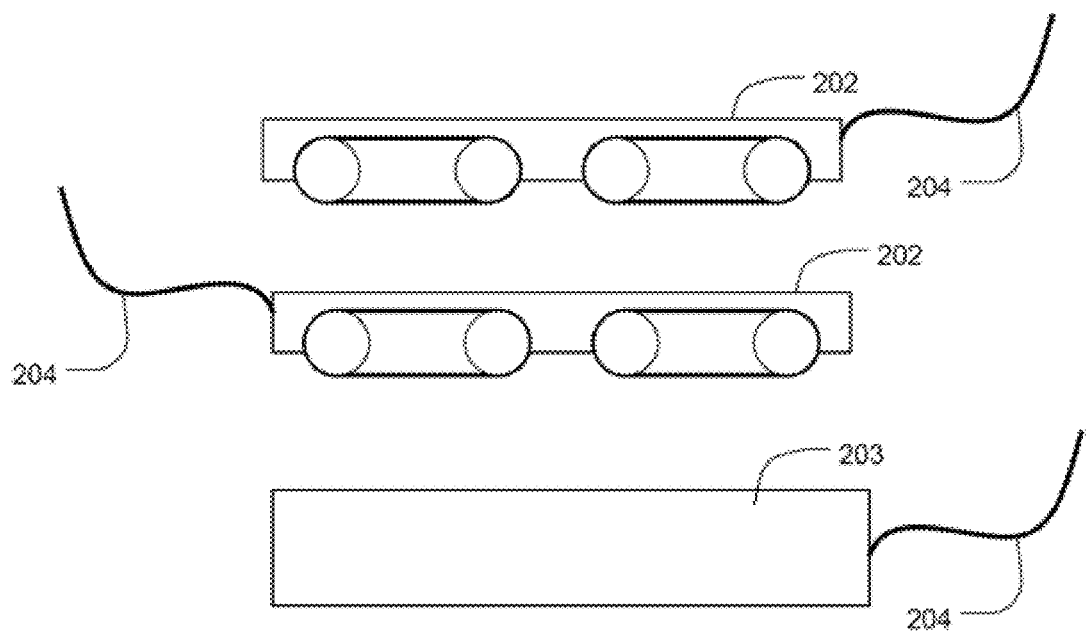
FIG. 2A provides an illustration of an ROV and its constituent components.
Figure 2B:
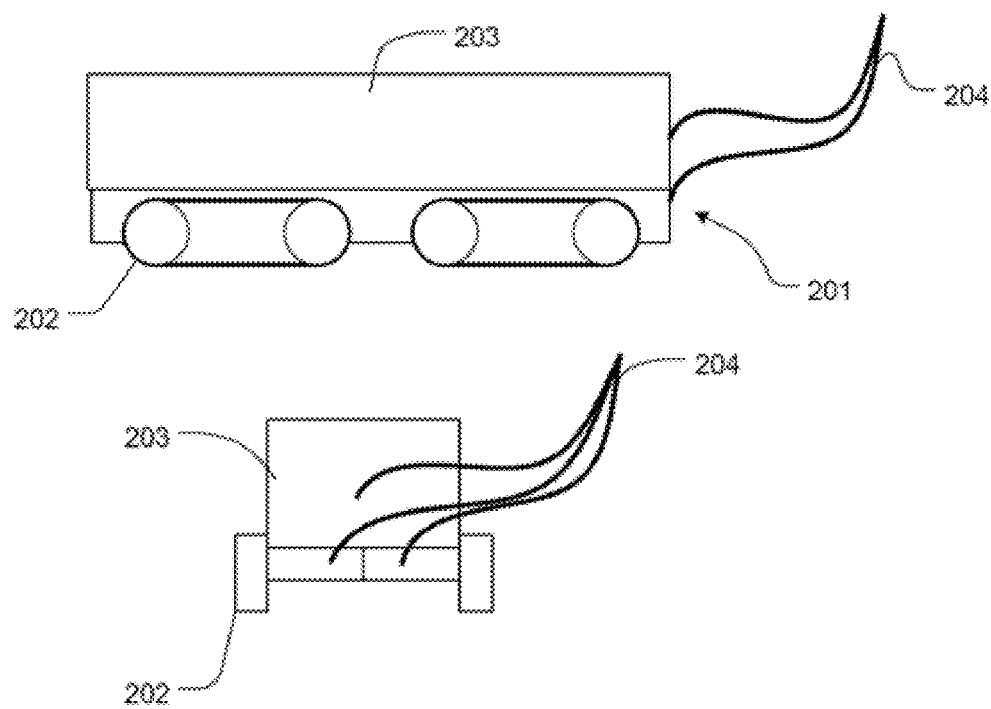
FIG. 2B shows an assembled ROV.

FIG. 2A provides an illustration of an ROV 201 and its constituent components. In this embodiment, ROV 201 is provided as three separate components, two tracked/wheeled portions 202 and a central portion 203 with an umbilical 204. FIG. 2B shows the assembled ROV 201, where the tracked/wheeled portions 202 have been bolted or snap linked to the central portion 203 to provide an operable ROV 201.

Once down the borehole and in the excavated region the ROV can move through the alluvium and engage with the mineral containing alluvial material. Navigation of the ROV may be automated, or the ROV may be remotely driven by an operator from the surface. Alternatively, the ROV may be capable of being both automated and remotely driven. Automated operation will be preferred where the ROV is conducting a time consuming operation that doesn't include much movement, such as shifting overburden or agitating wash material. In the case of remote operation by an operator, it is intended that a single operator could control the ROV. As the ROV will be automated some of the time, a remote operator may be able to monitor and control up to ten ROV's. The ROV will include a means to identify the surroundings; this may include sound and/or optical mechanisms such as sonar, ultrasound, or use of visual equipment such as lights and cameras.

The ROV is fitted with a drive mechanism including propulsion means, wherein the propulsion means may include tracks, wheels, or screw-propulsion for movement over a surface. The ROV may be fitted with either a single pair of propulsion means (e.g. a single track, wheel, or screw unit on at least two sides of the ROV); or alternatively the ROV may be fitted with multiple pairs of tracks, wheels or screws (e.g. front, middle, rear tracks, wheels, screws on at least two sides of the ROV). In an embodiment, the ROV is fitted with two pairs of propulsions means, e.g. has four tracks, wheels, or screw units.

To excavate alluvial material, the ROV operates as a suction dredge. The ROV is able to apply suction to draw the material in, and then up through the umbilical to a surface collection point. As discussed above, water may be provided to the ROV via the umbilical. If required, this water can be applied to break up the alluvial deposit and/or alter its consistency to create a slurry that can then be sucked into the ROV and extracted via the umbilical, e.g. the umbilical may include both a tube for supplying water, and a separate suction tube. In another arrangement, the ROV may contain a number of separate umbilicals that are dedicated to different tasks, an umbilical on a first component may supply control/electricals/hydraulics, an umbilical on the second component may provide pressurised water, and an umbilical on the third component may provide suction to withdraw and deliver to the surface slurrified alluvial material.

There are a range of methods through which an ROV can engage with the alluvial material. It is intended that the ROV is fitted with dredging apparatus, to allow the ROV to slurrify and withdraw alluvial material through suction, and provide the material via at least one of the umbilicals to a processing site above ground on the surface. The ROV may additionally be fitted with apparatus that is able to scrape or brush the bed rock to free or otherwise displace the alluvial deposits for dredging. In certain embodiments the ROV includes propulsion means, which can be operated in opposition to each other (e.g. one pair of propulsion means operates in the opposite direction from another pair of propulsion means). The effect of operating the propulsion means in opposition to each other in this manner scrapes or brushes the alluvial wash material overlying the bedrock loosening it so that it can be dredged. For example, the ROV may include a front drive mechanism engaged in the forward direction, and a rear drive mechanism engaged in the reverse direction, the operation of which is to displace alluvial material from the bedrock, by pushing material towards a central portion of the ROV for dredging. The ROV may also need to push or move large rocks that are present in the alluvium out of the way. To do this the ROV may be fitted with a shovel and/or blades.

The range of the ROV under the rock layer is at least in part limited by the umbilical. It is preferred that the range of the ROV is at least 100 m laterally from the borehole. More preferably, the range of the ROV is up to 300 m laterally from the borehole. Even more preferably, the range of the ROV is up to 500 m laterally from the borehole. Another factor that potentially limits the range of the ROV is the potential for roof collapse (the rock layer can be used as the roof). As the ROV extracts material from under the rock layer, a cavity is formed. There is potential for the roof (e.g. the rock layer) collapsing in on the ROV depending on its structural characteristics—these structural characteristics are likely to be site specific.

One method of providing additional support to the roof is to reinject the mineral depleted alluvium into the cavity. This may include forming a cement like material from a binder and the mineral depleted alluvium and then reinjecting it into the cavity where it solidifies and provides structural support.

In another embodiment, a binder may be directly injected from the surface into the alluvial material where in binds the alluvial material to form a concrete-like structure which provides support between the bedrock and rock roof. Cement may be used as the binder i.e. the cement may include lime and/or other additives mixed with the alluvium.

The ROV may also include a binder injection/spray hose. In this embodiment, binder can be supplied to the ROV via the umbilical. This allows the ROV to spray or inject binder (e.g. cement or other suitable binding agents) into the alluvial material to stabilise a particular area. For example, the ROV may be used to excavate a cavity and apply the binder agent to the walls/roof of that cavity for structural support. Additionally the ROV may be used to provide a binder/cement cap which then hardens/sets over an area.

As discussed, transport of alluvial material to the surface occurs through a dredging operation conducted by the ROV. The ROV is fitted with a suction device that draws the alluvial material into it, so that it can be transported to the surface for post-extraction treatment processes. The source of the suction may be from the above ground on the surface, e.g. suction is provided from an above ground location through the umbilical to the suction or dredging pipes on the ROV. One issue that can arise is blockages of the suction (dredging) pipes. To mitigate this, a screening mechanism will be present on the suction nozzle (which may literally be a mesh screen) to limit the size of particles that can be drawn into the pipe. However, screens are not completely effective at preventing ingress of large particles that have potential to block the pipe, particularly where these large particles have a high aspect ratio. It is intended that the pipe has a U-bend section to capture these large particles. The U-bend can be split open or alternatively radially opened out to release any large particles that have been retained in the U-bend. The splitting or radial opening may be done by actuators or using a reverse flow of water to physically open the U-bend, e.g. the reverse follow may provide actuation for unlocking catches in the pipe and open the U-bend. The opening and closing mechanism may be actuated by mechanical means, or through suction. The opening and closing mechanism may be spring assisted.

Figure 3A:
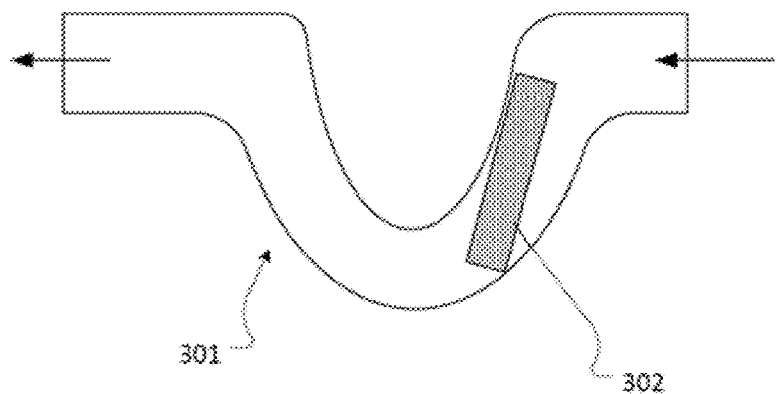
FIG. 3A provides an illustration of a U-bend pipe.
Figure 3B:
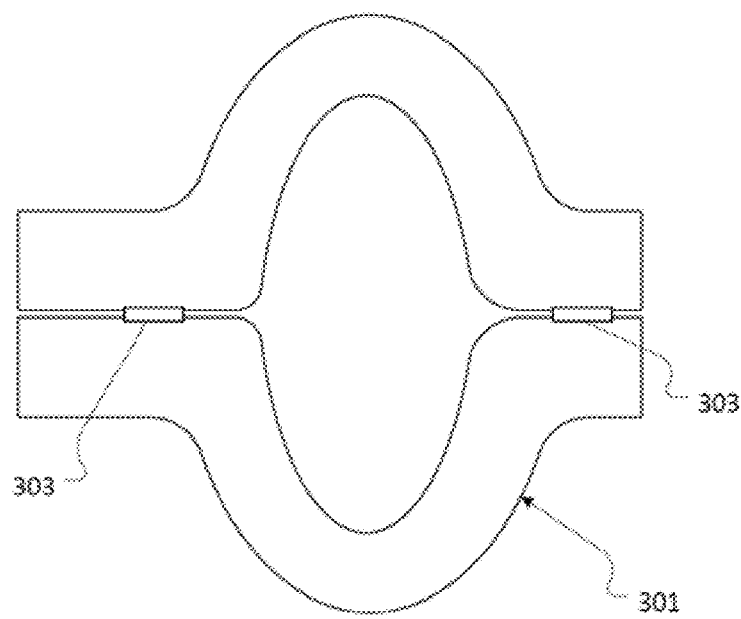
FIG. 3B provides an illustration of the opened U-bend pipe.
Figure 3B:
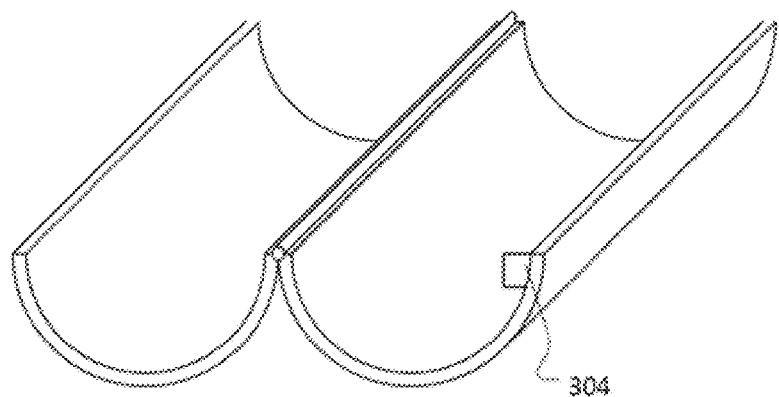

FIG. 3A provides an illustration of a U-bend pipe 301 with retained material 302 trapped inside. The U-bend pipe 301 includes hinges 303 in the closed position. FIG. 3B provides an illustration of the opened U-bend pipe 301 with the hinges 303 in the open position. The hinges 303 include a tab 304 has locked and an unlocked position. When the tab 304 is in the locked position, the hinges 303 are not free to move and the U-bend pipe 301 is held in the closed position. When the tab 304 is in the unlocked position, the hinges 303 are able to move and the U-bend pipe 301 can be opened to discharge any retained material 302.

The U-bend pipe may additionally include components to assist in dislodging the retained material. The U-bend pipe may include a piston which physically ejects retained material from the pipe, once the U-bend section of the pipe is opened. Alternatively, or in combination, air or water can be flushed through the pipe to eject the retained material once the U-bend section of the pipe is opened.

In yet another arrangement, the pipe may be lined with a rubber or plastic type material to provide wear resistance. Retained material may collect within the rubber/plastic lining. On opening the U-bend, the rubber/plastic lining may be inflated by water or gas at the interface between the inner layer of the pipe and the miter layer of the rubber/plastic lining. In this way, the lining may be used as a blow-out bag to dislodge the retained material.

Another factor that needs to be considered when conducting the mining and dredging operation is that the cavity formed beneath the rock layer is likely to be below the water table. Thus the cavity is likely to fill with water. The ROV therefore needs to be a submergible ROV that can operate in an underwater environment. The ROV may include aqueous propulsion means such as a propeller, fins, or water-jet. The water-jets may be externally powered by pumping water to the ROV via at least one umbilical. In the case where the ROV is submerged, the ROV may also need to be provided with a mechanism to overcome buoyancy forces. Accordingly, in one embodiment, additional weight can be provided to the ROV via at least one the umbilicals. The additional weight may be provided by transferring a heavy fluid or slurry, or by transporting heavy rocks or weights to the ROV. The ROV can then be made lighter by removing the additional weight.

It may also be advantageous to provide the ROV with a mechanism for rapidly deploying from the floor of the excavated region. The ROV may include an airbag (flotation bag) type system, which when deployed, lifts the ROV from the floor of the excavated region. The capital/operating costs of the ROV considering the danger of loss due to rock fall or slide in the overburden can be mitigated by use of these flotation bags to lift the ROV clear of a rock fall. If the flotation bags and a beacon were activated by a loss of a signal carried on the umbilical the permanent loss rate of ROVs should be considerably reduced.

The deployment may be as a result of a command received from an operator, or may be an automatic response. It is envisaged that if there is a loss of signal between the ROV and an operator or operations centre above ground on the surface, the ROV will deploy the airbags which will cause the ROV to move upwards, ideally re-establishing communication with the operator or operations centre. The airbag system may be particularly advantageous when the ROV becomes trapped beneath debris, e.g. as a result of a subterranean landslide or a collapsing roof. In the case of a collapsing roof triggering of the airbags can provide an upward force that may help to dislodge the debris, allowing the ROV to free itself. In some instances, accumulation of debris on top of the ROV may prevent communications between the ROV and operations centre. Automatic deployment of the airbag system in this case is particularly advantageous as it potentially allows the ROV to free itself from the debris and re-establish communications.

As mentioned previously, the invention is also directed to ancillary mining/dredging support processes such as detection of the material of interest in the alluvial deposit, and the use of this detection mechanism as a process control tool. Detectors of various types are often used to determine the presence of valuable minerals during prospecting. Two such patents (CA1215743 and CA1188734—the contents of which are hereby incorporated by reference) disclose the use of electrode probe for the detection of a metal or mineral in a geological formation. Essentially, these operate by detecting the "short circuiting" of conductive grains across a narrow gap between two mutually spaced electrodes.

These types of detectors are suitable for detecting a conductive material. This is because the sensors rely on a conductive material bridging between two electrodes on the probe to short-circuit the electrodes and generate a detection signal. Ideally these types of detectors are suitable for detecting native metal without a non-conducting oxidized layer on the surface.

These detectors have a number of shortcomings which renders them unsuitable for use in a mining process. The detectors disclosed in these documents are point probes that are manually inserted into the ground to detect the presence of an electrically conductive material at that specific location.

The detectors rely on physical contact between the electrode probe and the electrically conductive material. This means that the detectors are only able to detect electrically conductive material in a sampling location if that material is immediately adjacent to the electrodes. This means that the amount of material sampled at each location is very small, and is governed, in part, by the surface area of the electrode probe. If the electrode probe is small, then the amount of material sampled at each location is very little, which lowers the likelihood of detection of an electrically conductive material.

Furthermore, when the electrode portion of the detector is inserted into the ground, the electrically conductive material must align over the narrow gap between the two spaced electrodes in order to short circuit the electrodes and thus, generate a detection signal. This means of detection is heavily dependent on the concentration of the conductive material at each sampling location. If there is only a low amount of the conductive material in the soil, then there is a low likelihood that it would come into contact with the electrode probe, or even if it did come into contact with the probe that it would necessarily align correctly with the electrodes to generate a signal.

Another issue with these detectors is that they are only suitable for detecting surface deposits of a conductive material. If the conductive material resides at a reasonable depth below the surface, then these detectors cannot be used.

Additionally, the only information that the detectors report is whether the electrode probe has contacted an electrically conductive material or not. The detectors provide no data as to the amount or likely amount of the electrically conductive material in the ground.

Given the above, in order for any meaningful data to be generated, sampling needs to be conducted over potentially thousands of locations. This is both highly labour intensive and time consuming. Therefore these detectors are not suitable for use in a mining operation.

Despite the above, the inventors have advantageously found that the process used by these probes to identify minerals of interest can also be used as a process control tool to provide real time analysis of in a mining process.

U.S. Pat. No. 3,316,545 discloses a similar system using large co-planar electrodes with a meandering insulating space between them. Whilst such a system may be suitable for analysing material in a batch process it is unsuitable for use with continuous processes. First, the planar electrodes would be highly susceptible to wear. Second, the electrode configuration may generate sufficient levels of inductance in the detection circuit, that when a particle of material bridges the insulating space between electrodes, the level of current that flows will be significantly suppressed making detection of the particle difficult or impossible.

As discussed above, these types of detectors are suitable for detecting a conductive material such as gold, platinum group metals (such as ruthenium, rhodium, palladium, osmium, iridium, and platinum). Additionally, the sensors of the present invention are suitable for detecting hard rock copper and silver, and other metals that are in a conductive form, such as after a comminution process (which may break the oxidized layer, or result in comminuted metal particles without an oxidized layer). These materials would not be detected by a point sensor which is inserted into the ground such as those described in CA1215743 and CA1188734. This is because an initial treatment stage is required, such as comminution process, to expose conductive particles by breaking the oxidised layer and/or otherwise liberating conductive metal.

The inventor has found that by incorporating a detector including a series of spaced conductive electrodes in-line in a flow channel, the quantity of a material of interest in a mining stream can be determined. This is because the detectors are constantly in contact with a flow of mining material and therefore are continuously sampling the mining material as it flows by the detector. This means that the detector essentially provides continuous sampling of the mining material. There is a statistical correlation between the number of detection events and the concentration of the material of interest in the mining stream. Thus, even when the material of interest is present only at very low concentrations there is a statistical likelihood of a detection event occurring—although the time between detection events is expected to be large. Conversely, when the material of interest is present at high concentrations, there will be numerous and frequent detection events.

The detector may be calibrated using a mining stream (or other stream) containing a known concentration of a material of interest. For this known concentration, a frequency of detection events can be recorded. Further known concentrations of the material of interest may be used to provide additional data points to generate a calibration curve. When the detector is used in the field, the frequency of detection, events can be compared against the calibration curve to provide an indication of the concentration of the material of interest in the sample.

The calibration will, ideally, also factor in the expected shape and longest dimension of material of interest in the mining stream which can bridge the probe electrodes. Mineral processing is, in part, dependent on these properties as well as a number of other factors. It is likely that these parameters will need to be established through laboratory testing. It is expected that these parameters will vary depending on the source of the material of interest and whether any pre-processing has occurred. For example, it is expected that the shape and dimensions of gold particles will be different between alluvial or crushed hard rock deposits. Laboratory testing can be used to further calibrate or enhance the accuracy of an in-line monitoring process by, for example, providing feedback to the in-line monitoring system.

To improve the accuracy of the system, multiple detectors may be used in the flow channel. The use of multiple sensors increases the sensitivity of the system as it increases the likelihood of a detection event. The use of multiple detectors may be particularly beneficial in mining streams that include only a low concentration of the material of interest.

As will be appreciated, using a sensor system of the present type, which requires physical contact with a conductive particle or grain to detect its presence, even with a large sensor surface area and multiple sensors only a small fraction of the mining stream will be analysed. Therefore statistical methods will typically need to be employed to determine the concentration of the material of interest in the mining stream. A suitable statistical method may be through use of the Poisson distribution.

The inventor has also found that by incorporating rods of conductive electrodes in an inlet and outlet channel, the quantity of the material of interest in a mining stream can be determined and measured against the quantity of the material of interest in the mineral-depleted mining stream (e.g. after mineral extraction).

Ideally a number of rods of conductive electrode plates of different sized spacing are placed on an inlet stream to monitor the concentration of the material of interest in the stream prior to mineral extraction. These rods may be mounted on an inlet that is connected to an ROV, or may be mounted above ground in a pipe, channel, or other flow path that feeds a raw extracted mineral, which may be in the form of a slurry, to the mineral treatment processing plant.

The spacing between the Conductive electrode plates is important as different sized spacings will detect different sized particles. In order for particle detection to occur, a particle must come into contact with and bridge the gap between two electrode plates. This bridging results in a short-circuit being established between two electrode plates which results in a detection signal being registered. As such, larger electrode spacing provides for the detection of larger particles, but will limit detection of smaller particles as sufficiently small particles will be unable to bridge the spacing between electrodes.

The conductive electrodes may be formed from a conductive material that is hard to resist wear. Preferably, the hardness of the material is greater than the hardness of the mining material. Preferably the conductive material has a hardness of at least 7 on the Mohs scale, but preferably is even harder, say 9 or above. Suitable conductive materials include metal carbides in a metal matrix, such as tungsten carbide in a cobalt matrix, or silicon carbide. A wide range of hard material can be used is said electrodes if they are conductive (or can be made conductive by doping) including diamond, titanium carbide, titanium nitride, boron nitride, tungsten boride, molybdenum carbide. Such materials may be deposited on an electrode as a surface coating to provide better wear resistance. When the conductive material is silicon carbide, it is preferred that the silicon carbide is doped with a material to provide a surplus of electrons or holes, to improve the conductivity of the silicon carbide. Alternatively, the conductive electrodes may be formed from an conductive material that is resilient such as a conductive plastic or a plastic loaded with a conductive material such as a metal, for example silver. Unlike hard materials described above, such resilient materials are also known to withstand wear as they are able to absorb the impact of the abrasive mining feed material and undergo elastic deformation, then later release that energy and return to their original configuration. Electrodes of this type could, for example be formed from a material having Shore durometer harness of about D100 or less as defined in ASTM D22400-00.

The size, such as a length, of the conductive plates is also important. Larger conductive plates (plates having increased length, such as an increased radius in the case of cylindrical plates) will give rise to increased number and frequency of detection events due to a greater exposed surface area of the plate. The limitation on the size of each electrode is the likelihood of having temporally overlapping interactions with particles between the same set of plates. In some embodiments of the present invention the system cannot distinguish between a single particle bridging a pair of electrodes and multiple particles bridging a pair of electrodes. The likelihood of a particle interacting with a pair of electrodes is related to factors such as:

- electrode size (larger electrodes being more likely to detect a particle);
- concentration of the mineral of interest (higher concentration generally means more detection events, subject to particle size distribution as noted below);
- particle size distribution (a size distribution with more particles of a detectable size range will result in more detection events)
- flow rate of the material past the detector.

Accordingly the electrodes in the preferred embodiment are sized to avoid simultaneous detection events between electrode pairs.

A similar effect can be achieved by increasing the number of stacks of smaller plates (each with their own electronics) with a lower capacitance per stack. This may be useful for increasing detection events.

The current applied to the electrodes may be DC or AC. In the case of DC, ideally the voltage is less than 3V to prevent electrolysis and/or electrolysis of materials in the mining feed, which may result in gas generation which can cause dissolution of the electrode material. In some instances, gas generation (which doesn't lead to electrode dissolution) may be beneficial as, for example, dense gold will tend to be pushed through a $H_2$ gas layer (which form as microbubbles from nucleation) to provide a clearer signal.

With AC, higher voltages can be used with higher frequencies limiting gas generation and electrode dissolution. Higher frequencies up to the low kHz range, will generally require that stacks of smaller plates with reduced spacing, each with their own electronics to optimise capacitance effects.

Thus a first electrode is provided with a first face having a first surface area, and a corresponding electrode of opposite charge is provided with a second face having a second surface area. The electrodes are arranged in a stacked arrangement with a space there between. A mining material can flow through this space. The mining material has a residence time in this space that is proportional to the flow rate of the mining material. The residence time is configured so as to provide adequate time for the material of interest to interact and form an electrical connection between the first electrode and the corresponding electrode and to produce a detectable signal. The residence time can be changed by altering the flow rate of mining material through the space. Alternatively or additionally, the residence time may be altered by using electrodes having different surface areas. For example, electrodes with larger surface areas will bound a greater space through which material can flow, thus increasing residence time. Ideally a residence time is selected to enable sufficient opportunity for the electrical contact and thus the generation and detection of an electrical signal.

The electrode spacing may be provided by non-conductive spacers. The non-conductive spacers may be arranged in an alternating arrangement with the conductive electrode plates in a parallel layered type structure. The electrode spacing and/or the thickness of the non-conductive spacers will typically be in the range of 10 μm to 200 μm. The non-conductive spacers may be formed from an insulating material that is hard to resist wear. Preferably the non-conductive spacers are formed from a material that has a hardness of at least 7, but preferably 9 on the Mohs scale. Suitable insulating materials include non-conductive diamond, corundum ($Al_2O_3$, sapphire, ruby), or other hard powder (such as boron nitride) in epoxy. Alternatively, the non-conductive spacers may be formed from an insulating material that is resilient such as a nylon urethane. The insulating material will preferably have a resilience similar to its associated electrodes.

In some embodiments the non-conductive spacer could form part of a wall, floor and/or roof of the pipe or channel. For example, a series of electrode plates be mounted to a sidewall of the pipe or channel, with the electrodes projecting out horizontally from the sidewall. Similarly, from the floor or roof can additionally or alternatively be fitted with the electrodes projecting outwards into the flow of material. This arrangement means has an advantage that an extended sensor (e.g. in the form of a rod) does not project into the centre of the flow channel. Furthermore, as the velocity profile of flow increases towards the centre of a flow channel, use of a wall mounted set of electrodes can be advantageous, as lower flow at the edges means less wear also potentially reduces energy loss as the flow is less hindered.

Hard conductive electrodes may be paired with either hard or resilient non-conductive spacers. Similarly, resilient electrodes may be paired with either hard or resilient non-conductive spacers.

The resistance of the conductive electrodes and the non-conductive spacers to wear is more important when these elements are arranged in an inline monitoring process as compared with the devices disclosed in CA1215743 and CA1188734. The rods of the present invention are exposed to a flow of mining material that, during operation, is constantly flowing past the rods. This means that the rods of the present invention are constantly exposed to wear during operation. In contrast, the devices disclosed in CA1215743 and CA1188734 are simply inserted into the ground at various sampling points. These devices are not exposed to a constantly moving stream of mining material and therefore not subject to a high wear environment.

In an embodiment there are at least two stacks of rods having different sized spacing between the conductive plates. One stack of rods has large spacing, and one stack of rods has small spacing. This arrangement allows different sized mineral particles to be detected, e.g. the rod with the large spacing between conductive elements detects only large mineral particles, whereas the rod with small spacing between conductive elements additionally detects small mineral particles which may not be detected by the rod with large spacing between conductive elements.

For example, one rod stack has a spacing of 10 μm for detection of small conductive particles. The other rod stack has a spacing of 100 μm for detection of larger conductive particles. Each of the stacks may be provided with their own electronics.

It will be understood that more than two stacks can be used. For example a plurality of stacks may be used, some of which may have different sized electrodes and non-conductive elements. The exact number and configuration of the rod stacks in the plurality of stacks will be dependent on a number of factors such as the type of mining material and the physical and chemical properties of the material of interest.

Similarly, rods of conductive plates of different sizes are placed on an outlet stream from the mineral extraction plant to monitor the concentration of the material of interest in the stream after mineral extraction (which operates in the manner described above). This provides an indication on the quantity of the material of interest that is extracted in the mineral extraction stage, and thus provides data on the efficiency of the process.

The skilled person will appreciate that additional rods with varying degrees of spacing may be used depending on the expected size and size distribution of mineral particles within the alluvium.

Figure 4A:
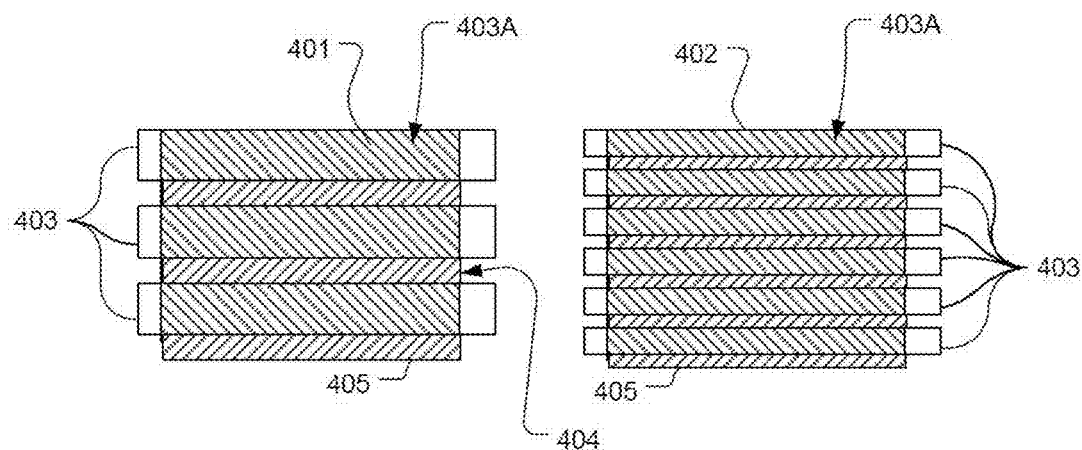
FIG. 4A provides an illustration of two rods with different sized spacing between conductive electrodes for determining the presence of a material of interest.

FIG. 4A provides an illustration of two rods 401, 402 stacked with conductive plates 403. The plurality of electrodes 403 each include an aperture 403A and a non-conducting shaft of the rod 401 or 402 extends through the apertures 403A. The first rod 401 has a non-conductive spacer 404 providing a large gap between the conductive plates 403. The second rod 402 has a non-conductive spacer 405 providing a small gap between the conductive plates 403.

Figure 4B:
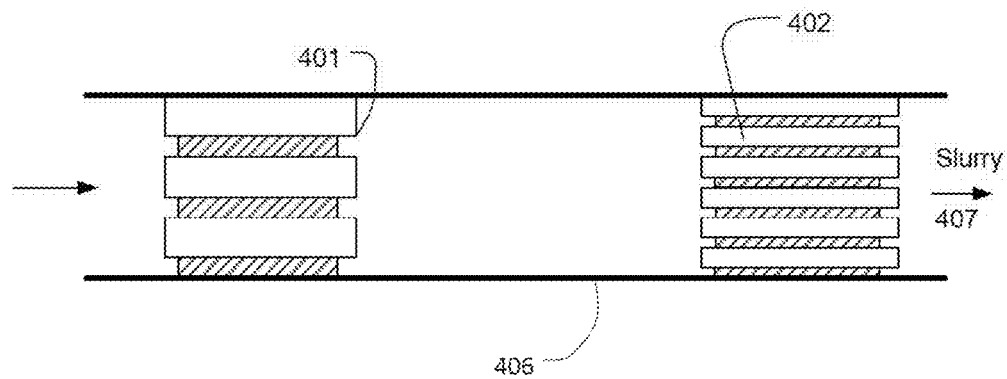
FIG. 4B shows an embodiment where the rods of FIG. 4A are incorporated in-line into a pipe.

FIG. 4B shows an embodiment where the rods 401, 402 are incorporated in-line into a pipe 406. Slurry 407 is pumped through the pipe 406 and passes through the spacers 204, 205 between the conductive plates 403. The rods detect the presence of) conductive particles (representing the material of interest—e.g. gold) as the slurry 407 passes by.

Figure 4C:
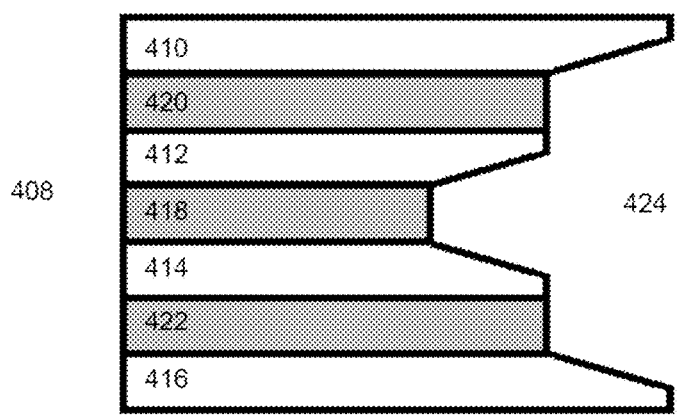
FIG. 4C shows an embodiment of a stack of electrodes.

FIG. 4C provides an illustration of an embodiment of a stack of electrodes 408. The stack of electrodes 408 includes two positive electrodes 410 and 412 and two negative electrodes 414 and 416. The positive and negative electrodes are separated by a non-conductive spacer element 418. Adjacent positive electrodes 410 and 412 are electrically isolated by a layer, which in this embodiment is a non-conductive spacer 420. Similarly, adjacent negative electrodes 414 and 416 are electrically isolated by a layer, which in this embodiment is a non-conductive spacer 422. Non-conductive layers 420 and 422 are not necessarily the same as non-conductive spacer layer 418. As can be seen in the Figure, the electrodes are of different sizes. Positive electrode 410 and negative electrode 416 are of the same size, with the outer perimeter of these electrodes extending beyond the outer perimeter of electrodes 412 and 414. In this arrangement, four separate circuits can be formed, a first circuit between electrodes 410 and 416, a second circuit between electrodes 410 and 414, a third circuit between electrodes 412 and 416, and a fourth circuit between electrodes 412 and 414.

The electrodes are arranged so as to form a flow space 424 for mining material there between.

As can be seen from FIG. 4C there are three different electrode spacings, a first electrode spacing between electrodes 410 and 416, a second electrode spacing between electrodes 410 and 414 and electrodes 412 and 416, and a third electrode spacing between electrodes 412 and 414. Due to these different electrode spacings, different size conductive particles will bridge between different electrodes and thus activate different circuits.

Large particles will form a bridge between electrodes 410 and 416 activating the first circuit. Medium sized particles will bridge between either electrodes 410 and 414 or 412 and 416 activating the second circuit or third circuits. Small particles will bridge between electrodes 412 and 414 activating the fourth circuit. In this way, information as to the size of conductive particles in a mining material can be obtained.

FIG. 4C also shows that each of the electrodes 410, 412, 414, and 416 has a bevelled surface. This bevelled surface helps to prevent particulate material from becoming wedged in the flow space 420.

Furthermore, the electrodes 410, 412, 414, and 416 are arranged so that the size of the electrodes sequentially decreases towards the centre of the stack of electrodes. This arrangement also helps to prevent material from becoming wedged or otherwise entrapped in the flow space 420.

The electrodes shown in FIG. 4C may be an entire stack, or only be one portion of the electrodes in a stack. In the latter case, further electrodes may be provided on either side of electrodes 410 and 416 (with appropriate non-conductive material therebetween). These further electrodes may be sequentially larger, thus expanding the range of sizes of the material of interest that can be detected. Alternatively, the further electrodes may be an additional stack of electrodes similar to those of FIG. 4C to provide a further stack with the same spacing adjacent to the electrode stack shown in FIG. 4C. Alternatively, the further stack may be different from the stack shown in FIG. 4C, and may include a different number or size of electrodes and non-conductive spaces.

Figure 4D:
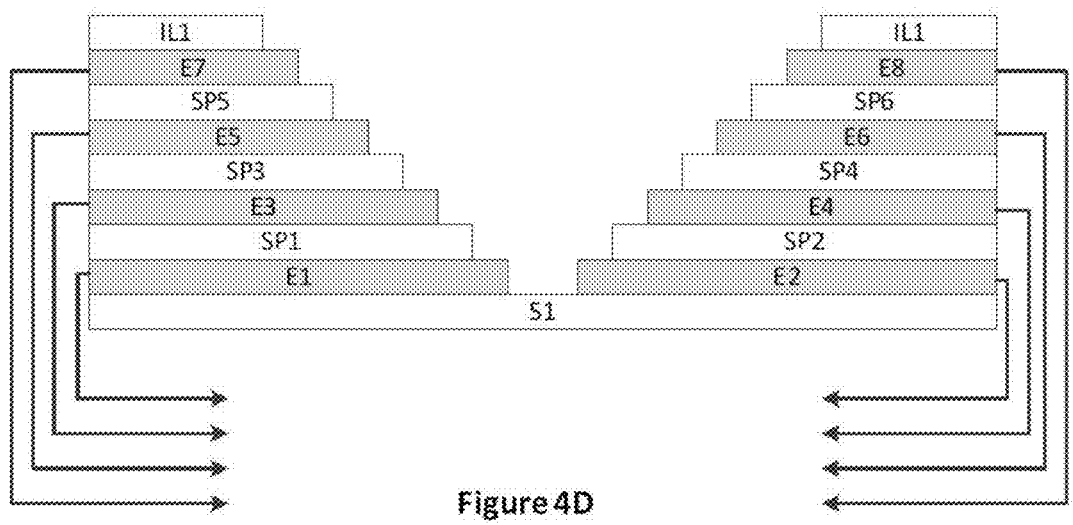
FIGS. 4D and 4E show two solid state electrode stacks able to be used in some embodiments of the present invention.
Figure 4E:
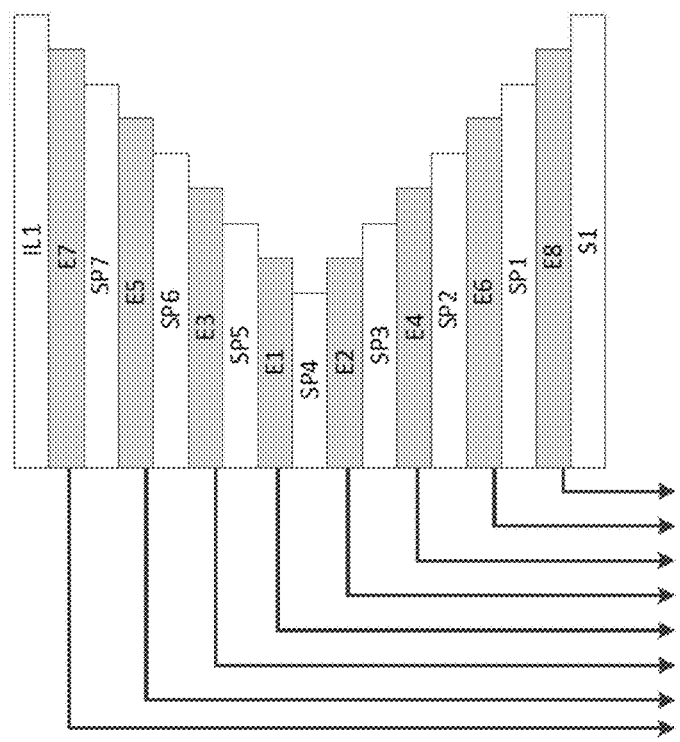

FIGS. 4D and 4E illustrate further embodiments of the present invention which are made using solid state fabrication techniques. In FIG. 4C the electrode stack is formed by depositing alternating conductive and insulating layers on a substrate S1, e.g. using chemical vapour deposition or the like. The electrode stack of FIG. 4C is formed as follows. The first layer deposited on substrates S1 is a conducting layer in which is formed electrodes E1 and E2. E1 and E2 do not touch each and as such the air gap between them forms a space between the electrodes E1 and E2. On top of this layer an insulating layer is formed to create spacers SP1 and SP2. The spacers SP1 and SP2 leave a small distance at the tips of E1 and E2 exposed to enable contact with mining material in use. This process is repeated to create conductive electrodes E3 and E4 on spacers SP1 and SP2. On top of E3 and E4 further insulating spacers are formed. This continues until the topmost conductive layer is deposited and electrodes formed. Over this topmost conductive layer an optional insulating cover can be deposited to form insulating layers IL1. Each electrode E1 to E8 is connected to the sensor electronics to enable the detection of conductive particles bridging between any pair of opposite polarity electrodes.

FIG. 4E is an alternative construction to that of FIG. 4D, in that the edges of the deposited layers are the exposed surfaces of the electrodes. In this example, a substrate S1 has deposited on it an conductive layer in which is formed E8. On top of this conductive layer an insulating layer is deposited. This is formed into spacer SP1. This process of depositing conductive layers and insulating layers continues until electrode E7 is formed. Over this layer an insulating layer IL1 is formed as a cover layer. As with the previous embodiment each electrode formed in the stack is connected to the sensor electronics to enable detection of a conductive particle bridging two of the electrodes.

It will be appreciated that any number of electrodes can be formed in this in any number of layers. For example, multiple electrodes can be formed in a single conductive layer (as illustrated by E1 and E2 in FIG. 4D).

A wide range of materials can be used to form electrodes, including diamond, silicon carbide, titanium carbide, titanium nitride, boron nitride, tungsten boride, molybdenum carbide, boron, rhenium diboride, stishovite, titanium diboride, carbonado. These materials can be deposited by vapour deposition (where appropriate) or incorporated as particles in a matrix.

Figure 5:
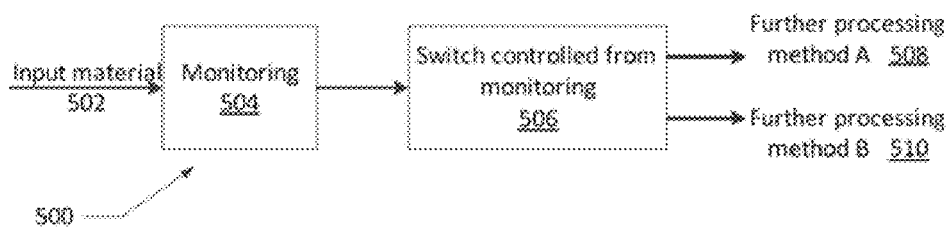
FIGS. 5 to 7 illustrate various embodiments of mining processes that include in-line monitors according to various aspects of the invention.

FIG. 5 illustrates an embodiment of a simple mining process 500 according to the present invention. An input material 502 is fed through an in-line monitoring system 504 a switch 506 decides where the mining stream is then fed. In the present example, there are two further processing steps, "step A" 508 and "step B" 510. However, it will be understood that further processing steps may be used.

In the present example the in-line monitoring system 504 monitors the input material 502 to determine a concentration of a material of interest in the input material 502. If the concentration of the material of interest is determined to be above a threshold value, the in-line monitoring system 504 uses the switch 506 to divert the input material 502 to further processing step A 508.

Further processing step A 508 may for example be a pre-treatment or extraction step. However, if the concentration of the material of interest is below a threshold value, the in-line monitoring system 504 uses the switch 506 to divert the input material 502 to further processing step B 510.

Further processing step B 510 may for example be a separation step which separates at least some of the gangue from the input material 502 to increase the concentration of the material of interest prior to further processing. Alternatively, step B may be to reject the input material as tailings due to the concentration of the material of interest being too low to be viable for extraction.

Advantageously, the in-line monitoring system 504 may be used to continuously monitor the input material 502 so that input material 502 that includes a concentration above the desired threshold can be diverted to further processing step A 508, and then if further input material 502 is found to be below the desired threshold, this can be diverted to further processing step B 510, Thus, the in-line monitoring system 504 can provide real time control of the mining process to improve the efficiency of the process.

Figure 6:
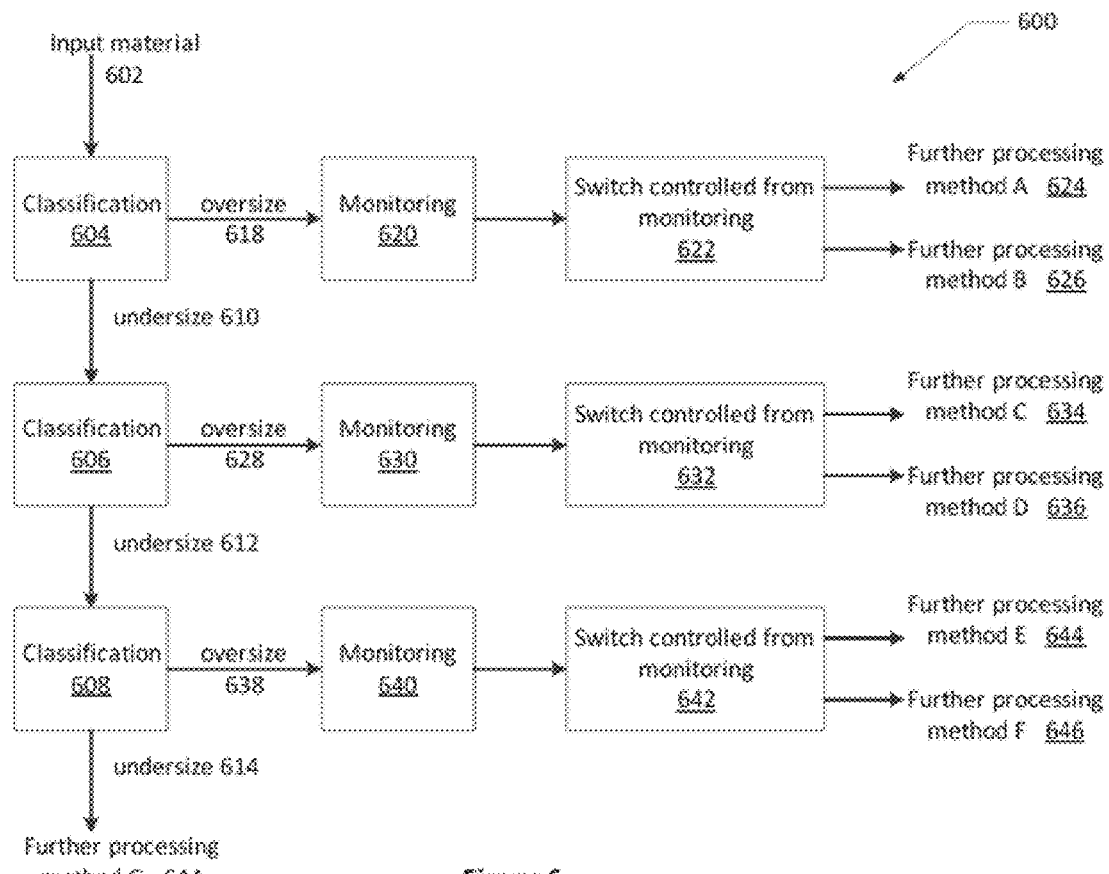

FIG. 6 illustrates another embodiment of a mining process 600 that takes an input material 602 and first separates this material according to a number of classification steps 604, 606, and 608. The undersized material 610 from classification step 604 is fed to classification step 606, the undersized material 612 from classification step 606 is fed to 608, the undersized material 614 from classification step 608 is fed to a further processing step 616 which may be a further classification step, a treatment step, or a disposal step.

It is important to note that a variety of classification steps may be used and that the sizes of the constituent components of the input material may vary depending on the nature of the classification step. For example, screening will separate all material into appropriate size ranges. However, other methods, such as the use of a cyclone separator (e.g. a hydrocyclone) will separate material depending on its shape and density. This may result in a situation where you have larger particles that are less dense paired with small particles of a more dense material. By way of example, the oversize/undersize split for a mix of gold and quartz particles may be gold 0.1 mm and quartz 1 mm.

The oversized material 618 from classification step 604 is fed through an in-line monitoring system 620 which communicates with a switch 622 to divert the material to either further processing step A 624 or further processing step B 626.

Similarly, the oversized material 628 from classification step 606 is fed through an in-line monitoring system 630 which communicates with a switch 632 to divert the material to either further processing step A 634 or further processing step B 636.

The oversized material 638 from classification step 608 is fed through an in-line monitoring system 640 which communicates with a switch 642 to divert the material to either further processing step A 644 or further processing step B 646.

The in-line monitoring steps 620, 630, 640, the switches 622, 632, 642, and the further processing methods 624, 626, 634, 636, 644, 646 may operate in a similar manner to that described above in respect of the process illustrated in FIG. 5.

An advantage of this system is that each of the monitoring systems 618, 628, 638 may be fitted with detectors that are optimised and/or calibrated to detect particles in a specific size regime. For example, the detectors may be optimised to have an electrode spacing that is tailored to the expected sizes of the material of interest in the classified input material.

Figure 7:
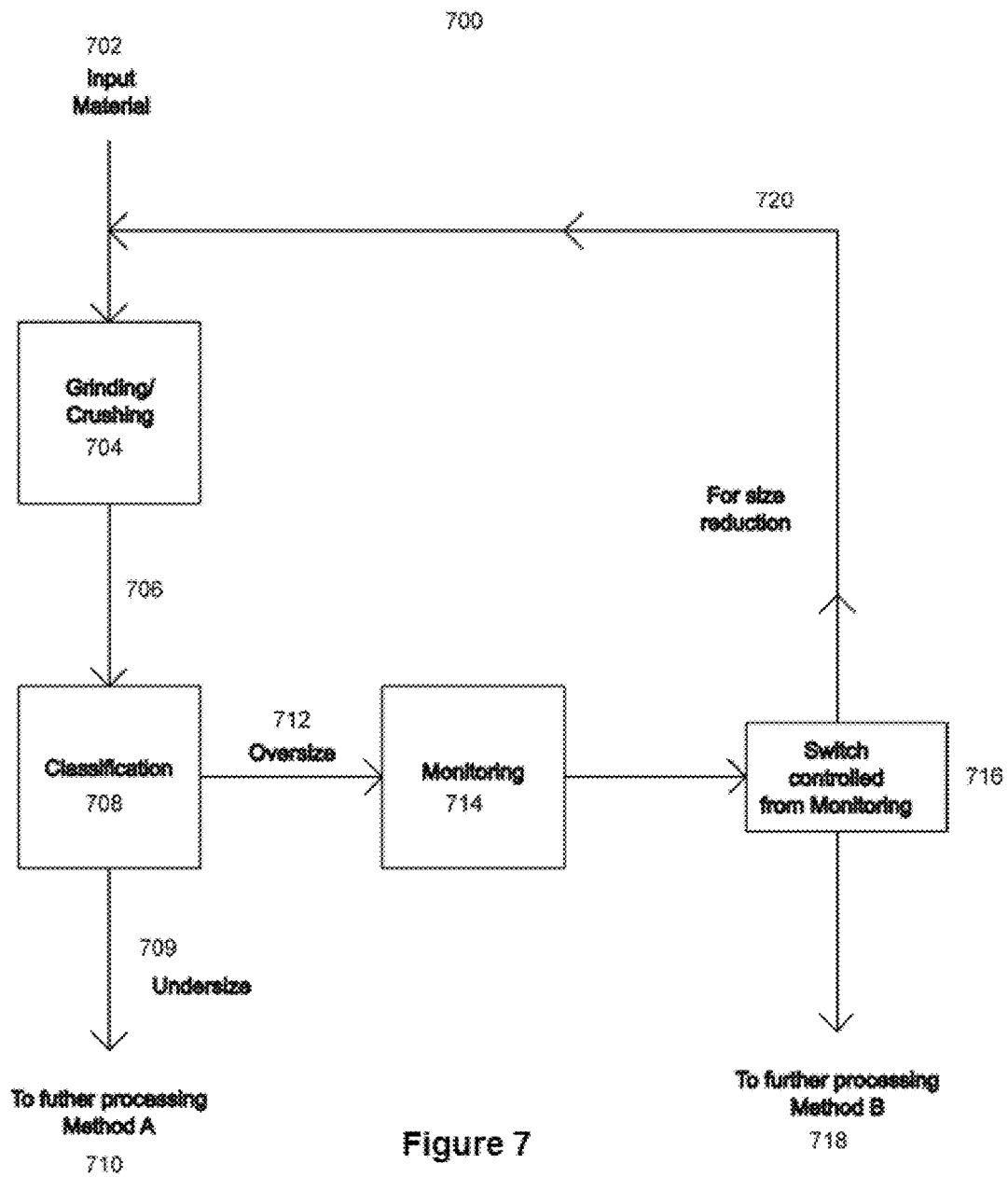

FIG. 7 illustrates another embodiment of a mining process 700. In this embodiment an input material 702 is fed to through a grinding/crushing process 704 where the input material is comminuted.

The comminuted material is then fed to a classifier 708 which may generally be as described above with respect to FIG. 6. The undersized material 709 is fed to further processing step A 710 which may be a further classification step, treatment step, processing step, or disposal step as generally described above with respect to the other embodiments. The oversized material 712 is fed through an in-line monitoring system 714.

The in-line monitoring system 714 communicates with switch 716 to divert material to either further processing step B 718, or to feed the material back to the grinding/crushing process 704 through a recycle loop 720. As above, further processing step B 718 may be a further classification step, treatment step, processing step, or disposal step as generally described above with respect to the other embodiments.

This embodiment is most likely to be useful with non-alluvial deposits, such as hard rock deposits.

While the invention may be applied generically for a range of minerals from alluvial deposits that are located underground beneath a rock layer, it will now generally be discussed in relation to alluvial gold deposits in a Deep Lead with a layer of basalt of at around 60 m deep overlaying the deposit. A typical section is shown in FIG. 5.

The first stage in Deep Lead Suction Dredging is to bore a hole to gain access to the alluvium. Currently vertical boring capacity to a depth of 100 meters appears limited (for economic reasons) to a 1.8 m diameter shaft in basalt. If necessary this shaft could be enlarged to any required size. A smaller test shaft would have to be drilled first to definitely establish the characteristics of the basalt. The shaft may have to be lined to prevent cross aquifer flow. There is also potentially, an issue of collapse of the shaft depending on the structural characteristics of the basalt.

The sands and clay overlying the wash can be considered as overburden and must be removed before excavating the wash. Initially it may be necessary to bring all of it to the surface but as mining proceeds along the lead it will be possible to backfill the lead without the considerable energy and maintenance costs of bringing this material to the surface. This is shown in FIG. 8.

Figure 8:
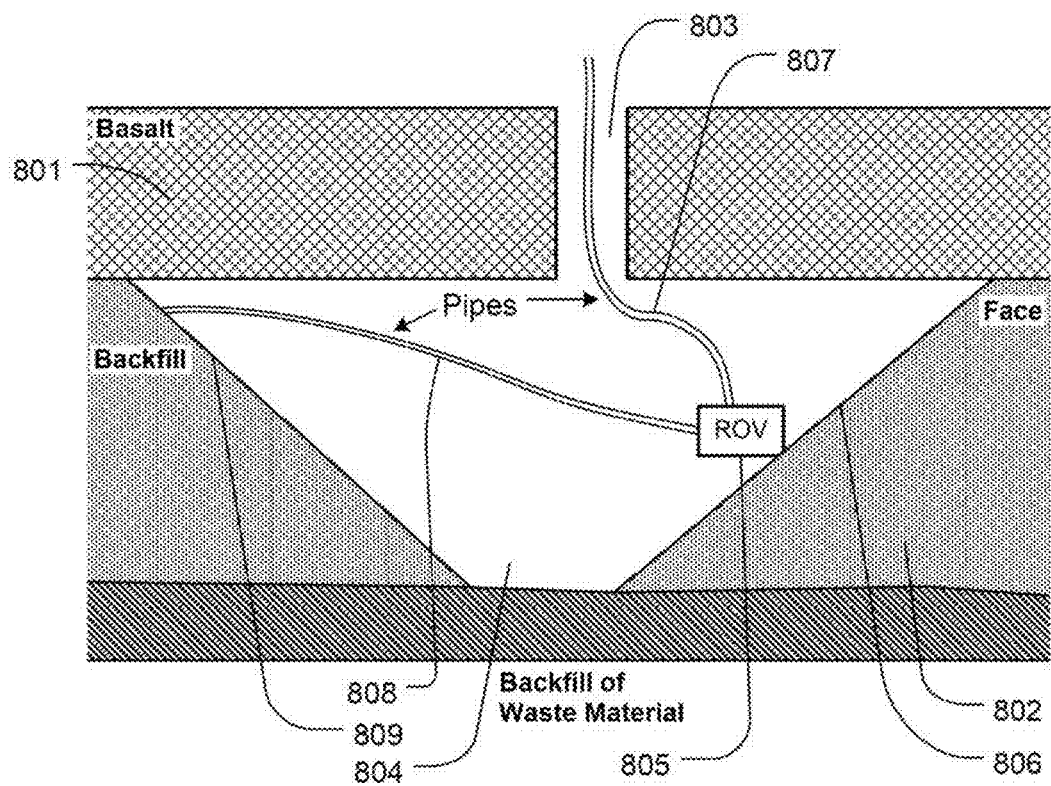
FIG. 8 shows an ROV mining a face of the alluvial deposit, and backfilling the excavated region.

FIG. 8 shows a basalt layer 801 overlying a gold containing alluvial deposit 802. A borehole 803 is drilled into the basalt layer 801. There is an excavated area 804 beneath borehole 803 in the basalt layer 801. An ROV 805 has an umbilical 806 which is in communication with an above ground facility on the surface (not shown). The ROV 805 mines from a alluvium face 806 by dredging alluvial material to the surface via the umbilical 807. The alluvial material is processed on the surface to extract the gold. Gold depleted alluvial material is then returned underground to the ROV 805 via the umbilical 803 and then via a pipe 808 deposited in a back fill area 809. Alternatively, if it is detected that some of the overburden material does not contain economically processable quantities of gold (for example with a detection device as described previously), the ROV 805 can dredge the material directly to the backfill 809 via the pipe 808 bypassing surface treatment.

It should be noted that the overburden material does contain gold and in some cases it may be worthwhile to bring it to the surface for treatment. A further point to consider is the gold content of the overburden and the low cost of Deep Lead Suction Dredging which may make the majority of the overburden payable. The main requirement of the overburden removal ROVs is to move a lot of material quickly. No great degree of positioning accuracy is required for this task. The forces on the ROV when moving material suggest that it be fixed to whatever bottom is available. Movement of the ROV can be achieved by tracks, swimming or a combination of both.

The wash differs from the overburden in larger size of material and in higher gold content. Some of the boulders will be too large to be picked up by any reasonable size of equipment and they will prevent access to some material. The basic approach will be to slurry the material with water jets and suck the slurry away. The ROV for wash mining well may be of a different design to that used for overburden removal.

As the wash extends for only part of the width of the lead the stable slope angle of the overburden will determine the stripping ratio together with the carrying thicknesses of overburden and wash. As the material (and aquifer) is wet and will have water moving through it the slope angle may be fairly low of the order 1:4 to 1:10. Another factor that needs to be considered is the strength and stability of the basalt roof, as this is important as it determines the width of cut which can be made at any one time. Apart from limiting the width of cut, pillars can be introduced to support the roof. These could be formed by large plastic bags pumped full of wet concrete.

In mining the wash the requirement is to slurry the wash by jets of water and remove the slurry by suction. One, concept for this is shown in FIG. 8 which is not unlike a hovercraft. Like a hovercraft the efficiency of the jets in slurrying could be possibly improved by use of a skirt and the efficiency of gold retrieval by use of dangling suction hoses. Putting the suction head and any cutters required on an ROV and having it move around at the end of a flexible hose radically increases the volume wash which can be extracted from a single borehole in comparison to other mining methods (such as straight dredging).

The size of the Wash Mining ROV is important as there is likely to be fairly big boulders in the lead which implies a large platform to slurry the area in and around them. With restriction of the size that can be taken down the shaft this suggests that the RV should be designed to go down the shaft in sections and be assembled underground.

Inevitably the Wash Mining ROV will encounter nuggets that it cannot extract by suction. Considering the value of these it would be desirable if it could locate these by remote sensing methods for extraction by a maintenance ROV.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. An in-line monitoring device for detecting a material of interest in a mining material, the device comprising:
    a plurality of electrodes including at least a first electrode which is a positive or a negative electrode, and a second electrode and a third electrode which are opposite in charge from the first electrode,
    the first electrode being separated from the second and third electrodes by a non-conductive space or spaces through which the mining material passes, wherein a spacing between adjacent electrodes is from 5 μm to 2000 μm;
    wherein the device is configured to detect the presence of the material of interest in the mining material as the mining material passes through the non-conductive space or spaces and forms an electrical connection between the first electrode and at least one of the second or third electrodes;

wherein the first electrode is configured to form with each of the second and third electrodes a different electrical circuit; and wherein the electrodes are arranged in a stack, with the first electrode being located at a first distance in the stack from the second electrode and at a second distance in the stack from the third electrode, the first distance being less than the second distance.

2. The in-line monitoring device of claim 1, wherein the second and third electrodes are electrically separated adjacent electrodes.

3. The in-line monitoring device of claim 1, wherein the electrodes are in a stepped arrangement, with the third electrode overhanging the second electrode to form the non-conductive space or spaces, the size and shape of the non-conductive space or spaces configured to minimize entrapment of the material of interest and/or the mining material.

4. The in-line monitoring device of claim 1, wherein a non-conductive spacer or spacers defines the non-conductive space or spaces, and the plurality of electrodes are arranged so that there is an overlap with at least a portion of the non-conductive spacer or spacers, the overlap defining the non-conductive space or spaces between at least the first electrode and the second and third electrodes.

5. The in-line monitoring device of claim 4, wherein the in-line monitoring device includes a plurality of positive and negative electrodes, the plurality of positive and negative electrodes separated from each other by the non-conductive space or spacers.

6. The in-line monitoring device of claim 5, wherein the plurality of electrodes are a plurality of conductive plates in a stacked relation with each other, the non-conductive spacer being a non-conductive plate located between adjacent conductive plates of opposite charge in the plurality of conductive plates in the stacked relation, and wherein adjacent plates of the same charge are electrically separated.

7. The in-line monitoring device of claim 5, wherein the non-conductive spacer is a portion of a flow channel through which the mining material is transported.

8. The in-line monitoring device of claim 7, wherein the plurality of electrodes are mounted to an outer wall portion of the flow channel.

9. The in-line monitoring device of claim 1, wherein the plurality of electrodes each comprise an aperture, and the device further comprises a non-conductive shaft, the non-conductive shaft extending through the apertures, the plurality of electrodes being mounted to the non-conductive shaft.

10. The in-line monitoring device of claim 1, wherein the plurality of electrodes are each formed from a material having a hardness of at least 7 on the Mohs scale.

11. The in-line monitoring device of claim 1, wherein the plurality of electrodes are each formed from a material having a resilience of about D100 or less.

12. The in-line monitoring device of claim 4, wherein the non-conductive spacer is formed from a material having a hardness of at least 7 on the Mohs scale.

13. The in-line monitoring device of claim 4, wherein the non-conductive spacer is formed from a material having a resilience of about D100 or less.

14. The device according to claim 1, wherein the device is used in an in-line monitoring process for detecting the material of interest in the mining material.

15. The device according to claim 7, wherein the device is installed in the flow channel for transporting the mining material.

16. A method for in-line monitoring of a mining material to detect a material of interest in the mining material, the method comprising:

providing the device according to claim 1 in a flow stream of a mining material; and using the device to monitor for the material of interest in the mining material.

17. An in-line monitoring process for detecting a material of interest in a mining material, the process comprising the steps of:

providing a device to a flow channel for the mining material, the device comprising:

a plurality of electrodes including at least three electrodes, a first electrode which is a positive or a negative electrode, and a second and a third electrode which are opposite in charge from the first electrode, the first electrode being separated from the second and third electrodes by a non-conductive space or spaces through which the mining material passes, wherein a spacing between adjacent electrodes is from 5 µm to 2000 µm;

wherein the device is configured to detect the presence of the material of interest in the mining material as the mining material passes through the non-conductive space or spaces and forms an electrical connection between the first electrode and at least one of the second or third electrodes;

wherein the first electrode is configured to form with each of the second and third electrodes a different electrical circuit;

wherein the electrodes are arranged in a stack, with the first electrode being located at a first distance in the stack from the second electrode and at a second distance in the stack from the third electrode, the first distance being less than the second distance; and transporting the mining material through the flow channel so that at least a portion of the mining material passes through the non-conductive space or spaces; and monitoring the portion of the mining material for the material of interest.

18. The process of claim 17, wherein the step of monitoring further comprises providing an output signal having a value that is indicative of a relative concentration of the material of interest in the mining material, wherein the value of the output signal is compared against a baseline value, and if the value of the output signal is below the baseline value the mining material is discarded, and if the value of the output signal is above the baseline value the mining material is retained.

19. The process of claim 18, wherein the value of the output signal is used to determine a downstream mining process.

20. The process of claim 17, wherein the device is provided on both an inlet stream to a mining process and an outlet stream from the mining process.

21. The process of claim 20, wherein the device on the inlet stream provides an inlet signal which is indicative of a relative concentration of the material of interest in the inlet stream, and the device on the outlet stream provides an outlet signal which is indicative of a relative concentration of the material of interest in the outlet stream; wherein the inlet signal and the outlet signal are correlated so as to provide an indication of an efficiency for an extraction of the material of interest from the mining material.

22. The process of claim 21, wherein the inlet stream to the mining process is at a location near to an extraction site of the mining material, and the outlet stream from the mining process is at a processing site where the material of interest can be extracted from the mining material.

\* \* \* \* \*